(12) United States Patent
Chory et al.

(10) Patent No.: US 6,245,969 B1
(45) Date of Patent: Jun. 12, 2001

(54) RECEPTOR KINASE, BIN1

(76) Inventors: Joanne Chory, 727 Hoska Dr., Del Mar, CA (US) 92014; Jianming Li, 4158 Decoro St., #34, San Diego, CA (US) 92122

(*) Notice: Subject to any disclaimer, the term of this patent is extended or adjusted under 35 U.S.C. 154(b) by 0 days.

(21) Appl. No.: 08/881,706

(22) Filed: Jun. 24, 1997

(51) Int. Cl.[7] .......................... C12N 15/29; C12N 15/54; C12N 15/82; A01H 5/00
(52) U.S. Cl. .......................... 800/290; 800/278; 800/286; 800/279; 800/301; 536/23.6; 536/24.5; 435/7.1; 435/7.8; 435/69.1; 435/320.1; 435/194; 435/419; 435/421; 435/468
(58) Field of Search ................................. 800/13, 21, 278, 800/286, 279, 290, 295, 298, 301; 536/23.5, 23.6, 24.31, 24.33, 24.5; 514/44; 435/468, 421, 320.1, 419, 194, 325, 7.8, 7.1, 69.1

(56) References Cited

PUBLICATIONS

TE Weier et al Botany pp. 315–319, 1982.*
PC Morris et al GenBank Accession #F13578, 1995.*
PC Morris et al GenBank Accession #F13577, 1995.*
Li et al., "A Putative Leucine–Rich Repeat Receptor Kinase Involved in Brassinosteriod Signal Transduction", *Cell*, vol. 90, pp. 929–938, Sep. 5, 1997.

* cited by examiner

*Primary Examiner*—David T. Fox
(74) *Attorney, Agent, or Firm*—Knobbe Martens Olson & Bear, LLP

(57) ABSTRACT

A novel plant steroid receptor, Bin1, is provided, as well as polynucleotides encoding Bin1. Bin1 polypeptide is useful in promoting increased plant yield and/or increased plant biomass. Genetically modified plants characterized as having increased yield and methods for producing such plants are also provided.

28 Claims, 3 Drawing Sheets

```
CTTCCACTTCCTCTGTAATGGTGGAACCAAAACCCTAGATTCCCCCTTTCATCTTCTCTA
CTTCCCACACTTTTCTCTCTCACAAACTCTTGAGAAATGAAGACTTTTTCAAGCTTCTTT
CTCTCTGTAACAACTCTCTTCTTCTTCTCCTTCTTTTCTCTTTCATTTCAAGCTTCACCA
TCTCAGTCTTTATACAGAGAAATCCATCAGCTTATAAGCTTCAAAGACGTTCTTCCTGAC
AAGAATCTTCTCCCAGACTGGTCTTCCAACAAAACCCGTGTACTTTCGATGGCGTTACT
TGCAGAGACGACAAAGTTACTTCGATTGATCTCAGCTCCAAGCCTCTCAACGTCGGATTC
AGTGCCGTGTCCTCGTCTCTCCTGTCTCTCACCGGATTAGAGTCTCTGTTTCTCAAAC
TCACACATCAATGGCTCCGTTTCTGGCTTCAAGTGCTCTGCTTCTTTAACCAGCTTGGAT
CTATCTAGAAACTCTCTTTCGGGTCCTGTAACGACTCTAACAAGCCTTGGTTCTTGCTCC
GGTCTGAAGTTTCTTAACGTCTCTTCCAATACACTTGATTTTCCCGGGAAAGTTTCAGGT
GGGTTGAAGCTAAACAGCTTGGAAGTTCTGGATCTTTCTGCGAATTCAATCTCCGGTGCT
AACGTCGTTGGTTGGGTTCTCTCCGATGGGTGTGGAGAGTTGAAACATTTAGCGATTAGC
GGAAACAAAATCAGTGGAGACGTCGATGTTTCTCGCTGCGTGAATCTCGAGTTTCTCGAT
GTTTCCTCCAACAATTTCTCCACTGGGATTCCTTTCCTCGGAGATTGCTCTGCTCTGCAA
CATCTTGACATCTCCGGGAACAAATTATCCGGCGATTTCTCCCGTGCTATCTCTACTTGC
ACAGAGCTCAAGTTGTTGAACATCTCTAGTAACCAATTCGTCGGACCAATCCCTCCGCTA
CCGCTTAAAAGTCTCCAATACCTCTCTCTGGCCGAGAACAAATTCACCGGCGAGATCCCT
GACTTTCTCTCCGGCGCGTGTGATACACTCACTGGTCTCGATCTCTCTGGAAATCATTTC
TACGGTGCGGTTCCTCCATTCTTCGGTTCATGTTCTCTTCTCGAATCACTCGCGTTGTCG
AGTAACAACTTCTCTGGCGAGTTACCGATGGATACGTTGTTGAAGATGAGAGGACTCAAA
GTACTTGATCTGTCTTTCAACGAGTTTTCCGGCGAATTACCGGAATCTCTGACGAATCTA
TCCGCTTCGTTGCTAACGTTAGATCTCAGCTCCAACAATTTCTCCGGTCCGATTCTCCCA
AATCTCTGCCAGAACCCTAAAAACACTCTGCAGGAGCTTTACCTTCAGAACAATGGCTTC
ACCGGGAAGATTCCACCGACTTTAAGCAACTGTTCTGAGCTGGTTTCGCTTCACTTGAGC
TTCAATTACCTCTCCGGGACAATCCCTTCGAGCTTAGGCTCTCTATCGAAGCTTCGAGAT
CTGAAACTATGGCTGAATATGTTAGAAGGAGAGATCCCTCAGGAGCTCATGTATGTCAAG
ACCTTAGAGACTCTGATCCTCGACTTCAACGATTTAACCGGTGAAATCCCTTCCGGTTTA
AGTAACTGTACCAATCTTAACTGGATTTCTCTGTCGAATAACCGGTTAACCGGTGAGATT
CCGAAATGGATTGGCCGGTTAGAGAATCTCGCTATCCTCAAGTTAAGCAACAATTCATTC
TCCGGGAACATTCCGGATGAGCTCGGCGACTGCAGAAGCTTAATCTGGCTTGATCTCAAC
ACCAATCTCTTCAATGGAACGATTCCGGCGGCGATGTTTAAACAATCCGGGAAAATCGCT
GCCAATTTCATCGCCGGTAAGAGGTACGTTTATATCAAAACGATGGGATGAAGAAAGAG
TGTCATGGAGCTGGTAATTTACTTGAGTTTCAAGGAATCAGATCCGAACAATTAAACCGG
CTTTCAACGAGGAACCCTTGTAATATCACTAGCAGAGTCTATGGAGGTCACACTTCGCCG
ACGTTTGATAACAATGGTTCGATGATGTTTCTGGACATGTCTTACAACATGTTGTCTGGA
TACATACCGAAGGAGATTGGTTCGATGCCTTATCTGTTTATTCTCAATTTGGGTCATAAC
GATATCTCTGGTTCGATTCCTGATGAGGTAGGTGATCTAAGAGGTTTAAACATTCTTGAT
CTTTCAAGCAATAAGCTCGATGGGAGGATTCCTCAGGCTATGTCAGCTCTTACTATGCTT
ACGGAAATCGATTTGTCGAATAATAATTTGTCTGGTCCGATTCCTGAGATGGGTCAGTTT
GAGACTTTTCCACCGGCTAAGTTCTTGAACAATCCTGGTCTCTGTGGTTATCCTCTTCCG
CGGTGTGATCCTTCAAATGCAGACGGTTATGCTCATCATCAGAGATCTCATGGAAGGAGA
CCAGCGTCCCTTGCTGGTAGTGTGGCGATGGATTGTTGTTCTCTTTTGTGTGTATATTT
GGGCTGATCCTTGTTGGTAGAGAGATGAGGAAGAGACGGAGAAAGAAAGAGGCGGAGTTG
GAGATGTATGCGGAAGGACATGGAAACTCTGGCGATAGAACTGCTAACAACACCAATTGG
AAGCTGACTGGTGTGAAAGAAGCCTTGAGTATCAATCTTGCTGCTTTCGAGAAGCCATTG
CGGAAGCTCACGTTTGCGGATCTTCTTCAGGCTACCAATGGTTTCCATAATGATAGTCTG
ATTGGTTCTGGTGGGTTTGGAGATGTTTACAAAGCGATTTTGAAAGATGGAAGCGCGGTG
GCTATCAAGAAACTGATTCATGTTAGCGGTCAAGGTGATAGAGAGTTCATGGCGGAGATG
GAAACCATTGGGAAGATCAAACATCGAAATCTTGTGCCTCTTCTTGGTTATTGCAAAGTT
```

FIGURE 1A

```
GGAGACGAGCGGCTTCTTGTTAATGAGGTTATGAAGTATGGAAGTTTAGAAGATGTTTTG
CAAGACCCCAAGAAAGGTGGGGTGAAACTTAAATTGTCCACACGGCGGAAGATTGCGATA
GGATCAGCTAGAGGGCTTGCTTTCCTTCACCACAACTGCAGTCCGCATATCATCCACAGA
GACATGAAATCCAGTAATGTGTTGCTTGATGAGAATTTGGAAGCTCGGGTTTCAGATTTT
GGCATGGCGAGGCTGATGAGTGCGATGGATACGCATTTAAGCGTCAGTACATTAGCTGGT
ACACCGGGTTACGTTCCTCCAGAGTATTACCAAAGTTTCAGGTGTTCAACAAAAGGAGAC
GTTTATAGTTACGGTGTGGTCTTACTCGAGCTACTCACGGGTAAACGGCCAACGGATTCA
CCGGATTTTGGAGATAACAACCTTGTTGGATGGGTGAAACAGCACGCAAAACTGCGGATT
AGCGATGTGTTTGACCCGGAGCTTATGAAGGAAGATCCAGCATTAGAGATCGAACTTTTA
CAACATTTAAAAGTTGCGGTTGCGTGTTTGGATGATCGGGCTTGGAGACGACCGACAATG
GTACAAGTCATGGCCATGTTTAAGGAGATACAAGCCGGGTCAGGGATAGATTCACAGTCA
ACGATCAGATCAATAGAGGATGGAGGGTTCAGTACAATAGAGATGGTTGATATGAGTATA
AAAGAAGTTCCTGAAGGAAAATTATGAGAGTTAGAAACAGAGCCAAAGCAGATTCTTTGA
ACATCAAAATCATCTAAGGGTCAGTCCGATTTTCCTTGGGTCTATTTTTTTGTATTTTC
TACTATATGCTAAGTGTATGTATCTATGTTATTTATACATAAGACGGATGTTTTTTTTTT
CGGGCTCGGTCGAATTGGGGGTGGTGGAGAATAGAACTAAGTAATAACTTTGTTAAGAAT
ATGTAAATATACAGTTTTTTGGGGAGGGATTTGTAATGTTTTCGTTTTTAGTTCTATGGA
AATTTCTACGTTGCTAACAAATTAAATTTATAATGAATCATGAAGAAACAAAGAGCCAAT
GTGTATTAAATTTCGACTGATCATGTTCATGTAAATGCACGTGACCTATTAATTCATTAT
TGTCGGAATTAATTTGGGGAATTC
```

FIGURE 1B

```
MKTFSSFFLSVTTLFFFSFFSLSFQASPSQSLYREIHQLISFKDVLPDKN
LLPDWSSNKNPCTFDGVTCRDDKVTSIDLSSKPLNVGFSAVSSSLLSLTG
LESLFLSNSHINGSVSGFKCSASLTSLDLSRNSLSGPVTTLTSLGSCSGL
KFLNVSSNTLDFPGKVSGGLKLNSLEVLDLSANSISGANVVGWVLSDGCG
ELKHLAISGNKISGDVDVSRCVNLEFLDVSSNNFSTGIPFLGDCSALQHL
DISGNKLSGDFSRAISTCTELKLLNISSNQFVGPIPPLPLKSLQYLSLAE
NKFTGEIPDFLSGACDTLTGLDLSGNHFYGAVPPFFGSCSLLESLALSSN
NFSGELPMDTLLKMRGLKVLDLSFNEFSGELPESLTNLSASLLTLDLSSN
NFSGPILPNLCQNPKNTLQELYLQNNGFTGKIPPTLSNCSELVSLHLSFN
YLSGTIPSSLGSLSKLRDLKLWLNMLEGEIPQELMYVKTLETLILDFNDL
TGEIPSGLSNCTNLNWISLSNNRLTGEIPKWIGRLENLAILKLSNNSFSG
NIPDELGDCRSLIWLDLNTNLFNGTIPAAMFKQSGKIAANFIAGKRYVYI
KNDGMKKECHGAGNLLEFQGIRSEQLNRLSTRNPCNITSRVYGGHTSPTF
DNNGSMMFLDMSYNMLSGYIPKEIGSMPYLFILNLGHNDISGSIPDEVGD
LRGLNILDLSSNKLDGRIPQAMSALTMLTEIDLSNNNLSGPIPEMGQFET
FPPAKFLNNPGLCGYPLPRCDPSNADGYAHHQRSHGRRPASLAGSVAMGL
LFSFVCIFGLILVGREMRKRRRKKEAELEMYAEGHGNSGDRTANNTNWKL
TGVKEALSINLAAFEKPLRKLTFADLLQATNGFHNDSLIGSGGFGDVYKA
ILKDGSAVAIKKLIHVSGQGDREFMAEMETIGKIKHRNLVPLLGYCKVGD
ERLLVNEVMKYGSLEDVLQDPKKGGVKLKLSTRRKIAIGSARGLAFLHHN
CSPHIIHRDMKSSNVLLDENLEARVSDFGMARLMSAMDTHLSVSTLAGTP
GYVPPEYYQSFRCSTKGDVYSYGVVLLELLTGKRPTDSPDFGDNNLVGWV
KQHAKLRISDVFDPELMKEDPALEIELLQHLKVAVACLDDRAWRRPTMVQ
VMAMFKEIQAGSGIDSQSTIRSIEDGGFSTIEMVDMSIKEVPEGKL
```

FIGURE 1C

SEQUENCE LISTING

```
<160> NUMBER OF SEQ ID NOS: 2

<210> SEQ ID NO 1
<211> LENGTH: 4104
<212> TYPE: DNA
<213> ORGANISM: Arabidopsis sp.
<220> FEATURE:
<221> NAME/KEY: CDS
<222> LOCATION: (97)..(3687)

<400> SEQUENCE: 1
cttccacttc ctctgtaatg gtggaaccaa aaccctagat tcccctttc atcttctcta      60 cttcccacac ttttctctct cacaaactct tgagaa atg aag act ttt tca agc     114
                                        Met Lys Thr Phe Ser Ser
                                        1               5 ttc ttt ctc tct gta aca act ctc ttc ttc ttc tcc ttc ttt tct ctt    162
Phe Phe Leu Ser Val Thr Thr Leu Phe Phe Phe Ser Phe Phe Ser Leu
            10                  15                  20 tca ttt caa gct tca cca tct cag tct tta tac aga gaa atc cat cag    210
Ser Phe Gln Ala Ser Pro Ser Gln Ser Leu Tyr Arg Glu Ile His Gln
        25                  30                  35
```

```
ctt ata agc ttc aaa gac gtt ctt cct gac aag aat ctt ctc cca gac    258
Leu Ile Ser Phe Lys Asp Val Leu Pro Asp Lys Asn Leu Leu Pro Asp
     40                  45                  50 tgg tct tcc aac aaa aac ccg tgt act ttc gat ggc gtt act tgc aga    306
Trp Ser Ser Asn Lys Asn Pro Cys Thr Phe Asp Gly Val Thr Cys Arg
 55                  60                  65                  70 gac gac aaa gtt act tcg att gat ctc agc tcc aag cct ctc aac gtc    354
Asp Asp Lys Val Thr Ser Ile Asp Leu Ser Ser Lys Pro Leu Asn Val
             75                  80                  85 gga ttc agt gcc gtg tcc tcg tct ctc ctg tct ctc acc gga tta gag    402
Gly Phe Ser Ala Val Ser Ser Ser Leu Leu Ser Leu Thr Gly Leu Glu
         90                  95                 100 tct ctg ttt ctc tca aac tca cac atc aat ggc tcc gtt tct ggc ttc    450
Ser Leu Phe Leu Ser Asn Ser His Ile Asn Gly Ser Val Ser Gly Phe
            105                 110                 115 aag tgc tct gct tct tta acc agc ttg gat cta tct aga aac tct ctt    498
Lys Cys Ser Ala Ser Leu Thr Ser Leu Asp Leu Ser Arg Asn Ser Leu
120                 125                 130 tcg ggt cct gta acg act cta aca agc ctt ggt tct tgc tcc ggt ctg    546
Ser Gly Pro Val Thr Thr Leu Thr Ser Leu Gly Ser Cys Ser Gly Leu
135                 140                 145                 150 aag ttt ctt aac gtc tct tcc aat aca ctt gat ttt ccc ggg aaa gtt    594
Lys Phe Leu Asn Val Ser Ser Asn Thr Leu Asp Phe Pro Gly Lys Val
                155                 160                 165 tca ggt ggg ttg aag cta aac agc ttg gaa gtt ctg gat ctt tct gcg    642
Ser Gly Gly Leu Lys Leu Asn Ser Leu Glu Val Leu Asp Leu Ser Ala
            170                 175                 180 aat tca atc tcc ggt gct aac gtc gtt ggt tgg gtt ctc tcc gat ggg    690
Asn Ser Ile Ser Gly Ala Asn Val Val Gly Trp Val Leu Ser Asp Gly
            185                 190                 195 tgt gga gag ttg aaa cat tta gcg att agc gga aac aaa atc agt gga    738
Cys Gly Glu Leu Lys His Leu Ala Ile Ser Gly Asn Lys Ile Ser Gly
200                 205                 210 gac gtc gat gtt tct cgc tgc gtg aat ctc gag ttt ctc gat gtt tcc    786
Asp Val Asp Val Ser Arg Cys Val Asn Leu Glu Phe Leu Asp Val Ser
215                 220                 225                 230 tcc aac aat ttc tcc act ggg att cct ttc ctc gga gat tgc tct gct    834
Ser Asn Asn Phe Ser Thr Gly Ile Pro Phe Leu Gly Asp Cys Ser Ala
                235                 240                 245 ctg caa cat ctt gac atc tcc ggg aac aaa tta tcc ggc gat ttc tcc    882
Leu Gln His Leu Asp Ile Ser Gly Asn Lys Leu Ser Gly Asp Phe Ser
            250                 255                 260 cgt gct atc tct act tgc aca gag ctc aag ttg ttg aac atc tct agt    930
Arg Ala Ile Ser Thr Cys Thr Glu Leu Lys Leu Leu Asn Ile Ser Ser
            265                 270                 275 aac caa ttc gtc gga cca atc cct ccg cta ccg ctt aaa agt ctc caa    978
Asn Gln Phe Val Gly Pro Ile Pro Pro Leu Pro Leu Lys Ser Leu Gln
280                 285                 290 tac ctc tct ctg gcc gag aac aaa ttc acc ggc gag atc cct gac ttt   1026
Tyr Leu Ser Leu Ala Glu Asn Lys Phe Thr Gly Glu Ile Pro Asp Phe
295                 300                 305                 310 ctc tcc ggc gcg tgt gat aca ctc act ggt ctc gat ctc tct gga aat   1074
Leu Ser Gly Ala Cys Asp Thr Leu Thr Gly Leu Asp Leu Ser Gly Asn
            315                 320                 325 cat ttc tac ggt gcg gtt cct cca ttc ttc ggt tca tgt tct ctt ctc   1122
His Phe Tyr Gly Ala Val Pro Pro Phe Phe Gly Ser Cys Ser Leu Leu
            330                 335                 340 gaa tca ctc gcg ttg tcg agt aac aac ttc tct ggc gag tta ccg atg   1170
Glu Ser Leu Ala Leu Ser Ser Asn Asn Phe Ser Gly Glu Leu Pro Met
```

-continued

|  |  |  |
|---|---|---|
| 345 | 350 | 355 |

| | |
|---|---|
| gat acg ttg ttg aag atg aga gga ctc aaa gta ctt gat ctg tct ttc<br>Asp Thr Leu Leu Lys Met Arg Gly Leu Lys Val Leu Asp Leu Ser Phe<br>360                      365                    370 | 1218 |
| aac gag ttt tcc ggc gaa tta ccg gaa tct ctg acg aat cta tcc gct<br>Asn Glu Phe Ser Gly Glu Leu Pro Glu Ser Leu Thr Asn Leu Ser Ala<br>375                      380                  385                  390 | 1266 |
| tcg ttg cta acg tta gat ctc agc tcc aac aat ttc tcc ggt ccg att<br>Ser Leu Leu Thr Leu Asp Leu Ser Ser Asn Asn Phe Ser Gly Pro Ile<br>                      395                  400                  405 | 1314 |
| ctc cca aat ctc tgc cag aac cct aaa aac act ctg cag gag ctt tac<br>Leu Pro Asn Leu Cys Gln Asn Pro Lys Asn Thr Leu Gln Glu Leu Tyr<br>          410                  415                  420 | 1362 |
| ctt cag aac aat ggc ttc acc ggg aag att cca ccg act tta agc aac<br>Leu Gln Asn Asn Gly Phe Thr Gly Lys Ile Pro Pro Thr Leu Ser Asn<br>425                      430                  435 | 1410 |
| tgt tct gag ctg gtt tcg ctt cac ttg agc ttc aat tac ctc tcc ggg<br>Cys Ser Glu Leu Val Ser Leu His Leu Ser Phe Asn Tyr Leu Ser Gly<br>440                      445                  450 | 1458 |
| aca atc cct tcg agc tta ggc tct cta tcg aag ctt cga gat ctg aaa<br>Thr Ile Pro Ser Ser Leu Gly Ser Leu Ser Lys Leu Arg Asp Leu Lys<br>455                      460                  465                  470 | 1506 |
| cta tgg ctg aat atg tta gaa gga gag atc cct cag gag ctc atg tat<br>Leu Trp Leu Asn Met Leu Glu Gly Glu Ile Pro Gln Glu Leu Met Tyr<br>                      475                  480                  485 | 1554 |
| gtc aag acc tta gag act ctg atc ctc gac ttc aac gat tta acc ggt<br>Val Lys Thr Leu Glu Thr Leu Ile Leu Asp Phe Asn Asp Leu Thr Gly<br>          490                  495                  500 | 1602 |
| gaa atc cct tcc ggt tta agt aac tgt acc aat ctt aac tgg att tct<br>Glu Ile Pro Ser Gly Leu Ser Asn Cys Thr Asn Leu Asn Trp Ile Ser<br>505                      510                  515 | 1650 |
| ctg tcg aat aac cgg tta acc ggt gag att ccg aaa tgg att ggc cgg<br>Leu Ser Asn Asn Arg Leu Thr Gly Glu Ile Pro Lys Trp Ile Gly Arg<br>          520                  525                  530 | 1698 |
| tta gag aat ctc gct atc ctc aag tta agc aac aat tca ttc tcc ggg<br>Leu Glu Asn Leu Ala Ile Leu Lys Leu Ser Asn Asn Ser Phe Ser Gly<br>535                      540                  545                  550 | 1746 |
| aac att ccg gat gag ctc ggc gac tgc aga agc tta atc tgg ctt gat<br>Asn Ile Pro Asp Glu Leu Gly Asp Cys Arg Ser Leu Ile Trp Leu Asp<br>                      555                  560                  565 | 1794 |
| ctc aac acc aat ctc ttc aat gga acg att ccg gcg gcg atg ttt aaa<br>Leu Asn Thr Asn Leu Phe Asn Gly Thr Ile Pro Ala Ala Met Phe Lys<br>          570                  575                  580 | 1842 |
| caa tcc ggg aaa atc gct gcc aat ttc atc gcc ggt aag agg tac gtt<br>Gln Ser Gly Lys Ile Ala Ala Asn Phe Ile Ala Gly Lys Arg Tyr Val<br>585                      590                  595 | 1890 |
| tat atc aaa aac gat ggg atg aag aaa gag tgt cat gga gct ggt aat<br>Tyr Ile Lys Asn Asp Gly Met Lys Lys Glu Cys His Gly Ala Gly Asn<br>600                      605                  610 | 1938 |
| tta ctt gag ttt caa gga atc aga tcc gaa caa tta aac cgg ctt tca<br>Leu Leu Glu Phe Gln Gly Ile Arg Ser Glu Gln Leu Asn Arg Leu Ser<br>615                      620                  625                  630 | 1986 |
| acg agg aac cct tgt aat atc act agc aga gtc tat gga ggt cac act<br>Thr Arg Asn Pro Cys Asn Ile Thr Ser Arg Val Tyr Gly Gly His Thr<br>                      635                  640                  645 | 2034 |
| tcg ccg acg ttt gat aac aat ggt tcg atg atg ttt ctg gac atg tct<br>Ser Pro Thr Phe Asp Asn Asn Gly Ser Met Met Phe Leu Asp Met Ser<br>          650                  655                  660 | 2082 |
| tac aac atg ttg tct gga tac ata ccg aag gag att ggt tcg atg cct | 2130 |

```
                                                                              -continued Tyr Asn Met Leu Ser Gly Tyr Ile Pro Lys Glu Ile Gly Ser Met Pro
            665                 670                 675 tat ctg ttt att ctc aat ttg ggt cat aac gat atc tct ggt tcg att     2178
Tyr Leu Phe Ile Leu Asn Leu Gly His Asn Asp Ile Ser Gly Ser Ile
        680                 685                 690 cct gat gag gta ggt gat cta aga ggt tta aac att ctt gat ctt tca     2226
Pro Asp Glu Val Gly Asp Leu Arg Gly Leu Asn Ile Leu Asp Leu Ser
695                 700                 705                 710 agc aat aag ctc gat ggg agg att cct cag gct atg tca gct ctt act     2274
Ser Asn Lys Leu Asp Gly Arg Ile Pro Gln Ala Met Ser Ala Leu Thr
                715                 720                 725 atg ctt acg gaa atc gat ttg tcg aat aat aat ttg tct ggt ccg att     2322
Met Leu Thr Glu Ile Asp Leu Ser Asn Asn Asn Leu Ser Gly Pro Ile
            730                 735                 740 cct gag atg ggt cag ttt gag act ttt cca ccg gct aag ttc ttg aac     2370
Pro Glu Met Gly Gln Phe Glu Thr Phe Pro Pro Ala Lys Phe Leu Asn
        745                 750                 755 aat cct ggt ctc tgt ggt tat cct ctt ccg cgg tgt gat cct tca aat     2418
Asn Pro Gly Leu Cys Gly Tyr Pro Leu Pro Arg Cys Asp Pro Ser Asn
760                 765                 770 gca gac ggt tat gct cat cat cag aga tct cat gga agg aga cca gcg     2466
Ala Asp Gly Tyr Ala His His Gln Arg Ser His Gly Arg Arg Pro Ala
775                 780                 785                 790 tcc ctt gct ggt agt gtg gcg atg gga ttg ttg ttc tct ttt gtg tgt     2514
Ser Leu Ala Gly Ser Val Ala Met Gly Leu Leu Phe Ser Phe Val Cys
                795                 800                 805 ata ttt ggg ctg atc ctt gtt ggt aga gag atg agg aag aga cgg aga     2562
Ile Phe Gly Leu Ile Leu Val Gly Arg Glu Met Arg Lys Arg Arg Arg
            810                 815                 820 aag aaa gag gcg gag ttg gag atg tat gcg gaa gga cat gga aac tct     2610
Lys Lys Glu Ala Glu Leu Glu Met Tyr Ala Glu Gly His Gly Asn Ser
        825                 830                 835 ggc gat aga act gct aac aac acc aat tgg aag ctg act ggt gtg aaa     2658
Gly Asp Arg Thr Ala Asn Asn Thr Asn Trp Lys Leu Thr Gly Val Lys
840                 845                 850 gaa gcc ttg agt atc aat ctt gct gct ttc gag aag cca ttg cgg aag     2706
Glu Ala Leu Ser Ile Asn Leu Ala Ala Phe Glu Lys Pro Leu Arg Lys
855                 860                 865                 870 ctc acg ttt gcg gat ctt ctt cag gct acc aat ggt ttc cat aat gat     2754
Leu Thr Phe Ala Asp Leu Leu Gln Ala Thr Asn Gly Phe His Asn Asp
                875                 880                 885 agt ctg att ggt tct ggt ggg ttt gga gat gtt tac aaa gcg att ttg     2802
Ser Leu Ile Gly Ser Gly Gly Phe Gly Asp Val Tyr Lys Ala Ile Leu
            890                 895                 900 aaa gat gga agc gcg gtg gct atc aag aaa ctg att cat gtt agc ggt     2850
Lys Asp Gly Ser Ala Val Ala Ile Lys Lys Leu Ile His Val Ser Gly
        905                 910                 915 caa ggt gat aga gag ttc atg gcg gag atg gaa acc att ggg aag atc     2898
Gln Gly Asp Arg Glu Phe Met Ala Glu Met Glu Thr Ile Gly Lys Ile
920                 925                 930 aaa cat cga aat ctt gtg cct ctt ctt ggt tat tgc aaa gtt gga gac     2946
Lys His Arg Asn Leu Val Pro Leu Leu Gly Tyr Cys Lys Val Gly Asp
935                 940                 945                 950 gag cgg ctt ctt gtt aat gag gtt atg aag tat gga agt tta gaa gat     2994
Glu Arg Leu Leu Val Asn Glu Val Met Lys Tyr Gly Ser Leu Glu Asp
                955                 960                 965 gtt ttg caa gac ccc aag aaa ggt ggg gtg aaa ctt aaa ttg tcc aca     3042
Val Leu Gln Asp Pro Lys Lys Gly Gly Val Lys Leu Lys Leu Ser Thr
            970                 975                 980
```

-continued

| | |
|---|---|
| cgg cgg aag att gcg ata gga tca gct aga ggg ctt gct ttc ctt cac<br>Arg Arg Lys Ile Ala Ile Gly Ser Ala Arg Gly Leu Ala Phe Leu His<br>            985                          990                      995 | 3090 |
| cac aac tgc agt ccg cat atc atc cac aga gac atg aaa tcc agt aat<br>His Asn Cys Ser Pro His Ile Ile His Arg Asp Met Lys Ser Ser Asn<br>1000                        1005                        1010 | 3138 |
| gtg ttg ctt gat gag aat ttg gaa gct cgg gtt tca gat ttt ggc atg<br>Val Leu Leu Asp Glu Asn Leu Glu Ala Arg Val Ser Asp Phe Gly Met<br>1015                        1020                        1025                        1030 | 3186 |
| gcg agg ctg atg agt gcg atg gat acg cat tta agc gtc agt aca tta<br>Ala Arg Leu Met Ser Ala Met Asp Thr His Leu Ser Val Ser Thr Leu<br>                        1035                        1040                        1045 | 3234 |
| gct ggt aca ccg ggt tac gtt cct cca gag tat tac caa agt ttc agg<br>Ala Gly Thr Pro Gly Tyr Val Pro Pro Glu Tyr Tyr Gln Ser Phe Arg<br>                        1050                        1055                        1060 | 3282 |
| tgt tca aca aaa gga gac gtt tat agt tac ggt gtg gtc tta ctc gag<br>Cys Ser Thr Lys Gly Asp Val Tyr Ser Tyr Gly Val Val Leu Leu Glu<br>1065                        1070                        1075 | 3330 |
| cta ctc acg ggt aaa cgg cca acg gat tca ccg gat ttt gga gat aac<br>Leu Leu Thr Gly Lys Arg Pro Thr Asp Ser Pro Asp Phe Gly Asp Asn<br>                        1080                        1085                        1090 | 3378 |
| aac ctt gtt gga tgg gtg aaa cag cac gca aaa ctg cgg att agc gat<br>Asn Leu Val Gly Trp Val Lys Gln His Ala Lys Leu Arg Ile Ser Asp<br>1095                        1100                        1105                        1110 | 3426 |
| gtg ttt gac ccg gag ctt atg aag gaa gat cca gca tta gag atc gaa<br>Val Phe Asp Pro Glu Leu Met Lys Glu Asp Pro Ala Leu Glu Ile Glu<br>                        1115                        1120                        1125 | 3474 |
| ctt tta caa cat tta aaa gtt gcg gtt gcg tgt ttg gat gat cgg gct<br>Leu Leu Gln His Leu Lys Val Ala Val Ala Cys Leu Asp Asp Arg Ala<br>                        1130                        1135                        1140 | 3522 |
| tgg aga cga ccg aca atg gta caa gtc atg gcc atg ttt aag gag ata<br>Trp Arg Arg Pro Thr Met Val Gln Val Met Ala Met Phe Lys Glu Ile<br>1145                        1150                        1155 | 3570 |
| caa gcc ggg tca ggg ata gat tca cag tca acg atc aga tca ata gag<br>Gln Ala Gly Ser Gly Ile Asp Ser Gln Ser Thr Ile Arg Ser Ile Glu<br>                        1160                        1165                        1170 | 3618 |
| gat gga ggg ttc agt aca ata gag atg gtt gat atg agt ata aaa gaa<br>Asp Gly Gly Phe Ser Thr Ile Glu Met Val Asp Met Ser Ile Lys Glu<br>1175                        1180                        1185                        1190 | 3666 |
| gtt cct gaa gga aaa tta tga gagttagaaa cagagccaaa gcagattctt<br>Val Pro Glu Gly Lys Leu<br>                        1195 | 3717 |
| tgaacatcaa aatcatctaa gggtcagtcc gattttcctt gggtctattt tttttgtatt | 3777 |
| ttctactata tgctaagtgt atgtatctat gttatttata cataagacgg atgtttttt | 3837 |
| tttcgggctc ggtcgaattg ggggtggtgg agaatagaac taagtaataa ctttgttaag | 3897 |
| aatatgtaaa tatacagttt tttggggagg gatttgtaat gttttcgttt ttagttctat | 3957 |
| ggaaatttct acgttgctaa caaattaaat ttataatgaa tcatgaagaa acaaagagcc | 4017 |
| aatgtgtatt aaatttcgac tgatcatgtt catgtaaatg cacgtgacct attaattcat | 4077 |
| tattgtcgga attaatttgg ggaattc | 4104 |

<210> SEQ ID NO 2
<211> LENGTH: 1196
<212> TYPE: PRT
<213> ORGANISM: Arabidopsis sp.

<400> SEQUENCE: 2

Met Lys Thr Phe Ser Ser Phe Phe Leu Ser Val Thr Thr Leu Phe Phe

```
  1               5                    10                        15
Phe Ser Phe Phe Ser Leu Ser Phe Gln Ala Ser Pro Ser Gln Ser Leu
             20                  25              30
Tyr Arg Glu Ile His Gln Leu Ile Ser Phe Lys Asp Val Leu Pro Asp
         35                  40              45
Lys Asn Leu Leu Pro Asp Trp Ser Ser Asn Lys Asn Pro Cys Thr Phe
     50                  55              60
Asp Gly Val Thr Cys Arg Asp Lys Val Thr Ser Ile Asp Leu Ser
 65                  70              75                      80
Ser Lys Pro Leu Asn Val Gly Phe Ser Ala Val Ser Ser Leu Leu
                 85                  90              95
Ser Leu Thr Gly Leu Glu Ser Leu Phe Leu Ser Asn Ser His Ile Asn
             100                 105             110
Gly Ser Val Ser Gly Phe Lys Cys Ser Ala Ser Leu Thr Ser Leu Asp
             115                 120             125
Leu Ser Arg Asn Ser Leu Ser Gly Pro Val Thr Thr Leu Thr Ser Leu
 130                 135             140
Gly Ser Cys Ser Gly Leu Lys Phe Leu Asn Val Ser Ser Asn Thr Leu
145                 150             155                      160
Asp Phe Pro Gly Lys Val Ser Gly Gly Leu Lys Leu Asn Ser Leu Glu
             165                 170             175
Val Leu Asp Leu Ser Ala Asn Ser Ile Ser Gly Ala Asn Val Val Gly
             180                 185             190
Trp Val Leu Ser Asp Gly Cys Gly Glu Leu Lys His Leu Ala Ile Ser
             195                 200             205
Gly Asn Lys Ile Ser Gly Asp Val Asp Val Ser Arg Cys Val Asn Leu
 210                 215             220
Glu Phe Leu Asp Val Ser Ser Asn Asn Phe Ser Thr Gly Ile Pro Phe
225                 230             235                      240
Leu Gly Asp Cys Ser Ala Leu Gln His Leu Asp Ile Ser Gly Asn Lys
             245                 250             255
Leu Ser Gly Asp Phe Ser Arg Ala Ile Ser Thr Cys Thr Glu Leu Lys
             260                 265             270
Leu Leu Asn Ile Ser Ser Asn Gln Phe Val Gly Pro Ile Pro Pro Leu
             275                 280             285
Pro Leu Lys Ser Leu Gln Tyr Leu Ser Leu Ala Glu Asn Lys Phe Thr
 290                 295             300
Gly Glu Ile Pro Asp Phe Leu Ser Gly Ala Cys Asp Thr Leu Thr Gly
305                 310             315                      320
Leu Asp Leu Ser Gly Asn His Phe Tyr Gly Ala Val Pro Pro Phe Phe
             325                 330             335
Gly Ser Cys Ser Leu Leu Glu Ser Leu Ala Leu Ser Ser Asn Asn Phe
             340                 345             350
Ser Gly Glu Leu Pro Met Asp Thr Leu Leu Lys Met Arg Gly Leu Lys
             355                 360             365
Val Leu Asp Leu Ser Phe Asn Glu Phe Ser Gly Glu Leu Pro Glu Ser
             370                 375             380
Leu Thr Asn Leu Ser Ala Ser Leu Leu Thr Leu Asp Leu Ser Ser Asn
385                 390             395                      400
Asn Phe Ser Gly Pro Ile Leu Pro Asn Leu Cys Gln Asn Pro Lys Asn
             405                 410             415
Thr Leu Gln Glu Leu Tyr Leu Gln Asn Asn Gly Phe Thr Gly Lys Ile
             420                 425             430
```

```
Pro Pro Thr Leu Ser Asn Cys Ser Glu Leu Val Ser Leu His Leu Ser
        435                 440                 445

Phe Asn Tyr Leu Ser Gly Thr Ile Pro Ser Ser Leu Gly Ser Leu Ser
450                 455                 460

Lys Leu Arg Asp Leu Lys Leu Trp Leu Asn Met Leu Glu Gly Glu Ile
465                 470                 475                 480

Pro Gln Glu Leu Met Tyr Val Lys Thr Leu Glu Thr Leu Ile Leu Asp
                485                 490                 495

Phe Asn Asp Leu Thr Gly Glu Ile Pro Ser Gly Leu Ser Asn Cys Thr
            500                 505                 510

Asn Leu Asn Trp Ile Ser Leu Ser Asn Asn Arg Leu Thr Gly Glu Ile
            515                 520                 525

Pro Lys Trp Ile Gly Arg Leu Glu Asn Leu Ala Ile Leu Lys Leu Ser
        530                 535                 540

Asn Asn Ser Phe Ser Gly Asn Ile Pro Asp Glu Leu Gly Asp Cys Arg
545                 550                 555                 560

Ser Leu Ile Trp Leu Asp Leu Asn Thr Asn Leu Phe Asn Gly Thr Ile
                565                 570                 575

Pro Ala Ala Met Phe Lys Gln Ser Gly Lys Ile Ala Ala Asn Phe Ile
            580                 585                 590

Ala Gly Lys Arg Tyr Val Tyr Ile Lys Asn Asp Gly Met Lys Lys Glu
        595                 600                 605

Cys His Gly Ala Gly Asn Leu Leu Glu Phe Gln Gly Ile Arg Ser Glu
        610                 615                 620

Gln Leu Asn Arg Leu Ser Thr Arg Asn Pro Cys Asn Ile Thr Ser Arg
625                 630                 635                 640

Val Tyr Gly Gly His Thr Ser Pro Thr Phe Asp Asn Asn Gly Ser Met
                645                 650                 655

Met Phe Leu Asp Met Ser Tyr Asn Met Leu Ser Gly Tyr Ile Pro Lys
                660                 665                 670

Glu Ile Gly Ser Met Pro Tyr Leu Phe Ile Leu Asn Leu Gly His Asn
        675                 680                 685

Asp Ile Ser Gly Ser Ile Pro Asp Glu Val Gly Asp Leu Arg Gly Leu
        690                 695                 700

Asn Ile Leu Asp Leu Ser Ser Asn Lys Leu Asp Gly Arg Ile Pro Gln
705                 710                 715                 720

Ala Met Ser Ala Leu Thr Met Leu Thr Glu Ile Asp Leu Ser Asn Asn
                725                 730                 735

Asn Leu Ser Gly Pro Ile Pro Glu Met Gly Gln Phe Glu Thr Phe Pro
            740                 745                 750

Pro Ala Lys Phe Leu Asn Asn Pro Gly Leu Cys Gly Tyr Pro Leu Pro
        755                 760                 765

Arg Cys Asp Pro Ser Asn Ala Asp Gly Tyr Ala His His Gln Arg Ser
        770                 775                 780

His Gly Arg Arg Pro Ala Ser Leu Ala Gly Ser Val Ala Met Gly Leu
785                 790                 795                 800

Leu Phe Ser Phe Val Cys Ile Phe Gly Leu Ile Leu Val Gly Arg Glu
                805                 810                 815

Met Arg Lys Arg Arg Arg Lys Lys Glu Ala Glu Leu Glu Met Tyr Ala
                820                 825                 830

Glu Gly His Gly Asn Ser Gly Asp Arg Thr Ala Asn Asn Thr Asn Trp
            835                 840                 845
```

```
Lys Leu Thr Gly Val Lys Glu Ala Leu Ser Ile Asn Leu Ala Ala Phe
    850             855                 860

Glu Lys Pro Leu Arg Lys Leu Thr Phe Ala Asp Leu Leu Gln Ala Thr
865             870             875                 880

Asn Gly Phe His Asn Asp Ser Leu Ile Gly Ser Gly Phe Gly Asp
                885                 890                 895

Val Tyr Lys Ala Ile Leu Lys Asp Gly Ser Ala Val Ala Ile Lys Lys
            900             905                 910

Leu Ile His Val Ser Gly Gln Gly Asp Arg Glu Phe Met Ala Glu Met
        915                 920                 925

Glu Thr Ile Gly Lys Ile Lys His Arg Asn Leu Val Pro Leu Leu Gly
    930             935                 940

Tyr Cys Lys Val Gly Asp Glu Arg Leu Leu Val Asn Glu Val Met Lys
945             950                 955                 960

Tyr Gly Ser Leu Glu Asp Val Leu Gln Asp Pro Lys Lys Gly Gly Val
                965                 970                 975

Lys Leu Lys Leu Ser Thr Arg Arg Lys Ile Ala Ile Gly Ser Ala Arg
            980                 985                 990

Gly Leu Ala Phe Leu His His Asn Cys Ser Pro His Ile Ile His Arg
            995             1000                1005

Asp Met Lys Ser Ser Asn Val Leu Leu Asp Glu Asn Leu Glu Ala Arg
        1010                1015                1020

Val Ser Asp Phe Gly Met Ala Arg Leu Met Ser Ala Met Asp Thr His
025                 1030                1035                1040

Leu Ser Val Ser Thr Leu Ala Gly Thr Pro Gly Tyr Val Pro Pro Glu
                1045                1050                1055

Tyr Tyr Gln Ser Phe Arg Cys Ser Thr Lys Gly Asp Val Tyr Ser Tyr
            1060                1065                1070

Gly Val Val Leu Leu Glu Leu Leu Thr Gly Lys Arg Pro Thr Asp Ser
        1075                1080                1085

Pro Asp Phe Gly Asp Asn Asn Leu Val Gly Trp Val Lys Gln His Ala
    1090                1095                1100

Lys Leu Arg Ile Ser Asp Val Phe Asp Pro Glu Leu Met Lys Glu Asp
105                 1110                1115                1120

Pro Ala Leu Glu Ile Glu Leu Leu Gln His Leu Lys Val Ala Val Ala
                1125                1130                1135

Cys Leu Asp Asp Arg Ala Trp Arg Arg Pro Thr Met Val Gln Val Met
            1140                1145                1150

Ala Met Phe Lys Glu Ile Gln Ala Gly Ser Gly Ile Asp Ser Gln Ser
        1155                1160                1165

Thr Ile Arg Ser Ile Glu Asp Gly Gly Phe Ser Thr Ile Glu Met Val
    1170                1175                1180

Asp Met Ser Ile Lys Glu Val Pro Glu Gly Lys Leu
185                 1190                1195
```

RECEPTOR KINASE, BIN1

This invention was made with Government support under Grant No. DIR 9116923 awarded by the National Science Foundation and Grant No. 93-373019125 awarded by the U.S. Department of Agriculture. The Government has certain rights in this invention.

FIELD OF THE INVENTION

The present invention relates generally to plant genetic engineering, and specifically to a novel gene useful for producing genetically engineered plants characterized as having a phenotype of increased crop yield, enhanced disease resistance and longer-lived vegetative growth phase.

BACKGROUND OF THE INVENTION

The brassinosteroids are a unique class of biologically active natural products that possess plant steroidal hormone activity. Their low effective concentrations for use on crops make them environmentally safe and those brassinosteroids used on a large scale are generally non-toxic. At the physiological level, brassinosteroids elicit many changes and could represent a new class of hormones in plants. The economic aspects of the brassinosteroids may have worldwide effects. For example, the brassinosteroids can be used as plant protectants from both pesticide and environmental adversity. In addition, brassinosteroids appear to be useful for insect control. Further, brassinosteroids may regulate some stage of the reproductive cycle in plants, thereby providing the means to increase or decrease the reproductive process. For example, in certain horticultural crops, it may be desirable to eliminate the flowering process to ensure continuous production of other tissues such as leaves, bulbs and other storage organs. This modulation of the reproductive process could be important in the control of certain seed bearing weeds, where cessation of the flowering cycle eliminates future generations. Brassinosteroids also appear to stimulate root growth, and external application causes no deformity of plants.

Brassinosteroids qualify for classification as biochemical pesticides. Such pesticides are generally distinguished from conventional chemical pesticides by their unique modes of action, low effective concentration, target species, and specificity. Historically, the brassinosteroids have not been used in actual agricultural applications due to the expense involved in producing them as well as the difficulty in purifying them.

It is known that once hormones, such as glucocorticoid, enter a cell, they bind to specific receptor proteins, thereby creating a ligand/receptor complex. The binding of the hormone to the receptor is believed to initiate an allosteric alteration of the receptor protein. As a result, it is believed that the ligand/receptor complex is capable of binding with high affinity to certain specific sites on the chromatin nucleic acid. Such sites, which are known as response elements, modulate expression of nearby target gene promoters.

Recent evidence indicates that in addition to intracellular, genomic effects, steroids also exhibit non-genomic effects, i.e., they affect the surface of cells and alter ion permeability, as well as release of neurohormones and neurotransmitters. Steroids such as estrogens and adrenal steroids and their naturally produced and synthetic analogs have shown membrane effects. In view of the foregoing, it appears that steroids may cause synergistic interactions between non-genomic and genomic responses resulting in alterations in neural activity or certain aspects of oocyte and spermatozoa maturation, for example.

SUMMARY OF THE INVENTION

Although steroid hormones are important for animal development, the physiological role of plant steroids is largely unknown. The present invention is based on the discovery of the Bin1 gene, which encodes a polypeptide that functionsas a receptor kinase and is involved in the brassinolide response pathway.

In a first embodiment, the invention provides Bin1 polypeptide which binds to brassinosteroids and isolated polynucleotide sequences encoding Bin1.

In another embodiment, the invention provides a method for producing a genetically modified plant characterized as having increased yield as compared to a wild-type plant. The method is based on introducing at least one nucleic acid sequence encoding Bin1 polypeptide, operably associated with a promoter, to a plant cell to obtain a transformed plant cell and producing a plant from the transformed plant cell. Such genetically modified plants may exhibit increased crop yield or increased biomass.

In yet another embodiment, the invention provides a method for producing a plant characterized as having increased yield, by contacting a plant having a native bin1 gene operably linked to its native promoter, with a promoter-inducing amount of an agent which induces bin1 gene expression, wherein elevation of bin1 gene expression results in production of a plant having increased yield as compared to a plant not contacted with the inducing agent. Thus, transcription factors or chemical agents may be used to increase expression of Bin1 in a plant, in order to provide increased yield. Alternatively, plants genetically transfromed with Bin1 can also be contacted with a promoter-inducing amount of an agent which elevates Bin1 expression to obtain plants having increased yield.

BRIEF DESCRIPTION OF THE DRAWINGS

FIGS. 1A–C show the nucleotide (A,B) and deduced amino acid (C) sequences of Bin1 of the invention (SEQ ID NO:1 and SEQ ID NO:2, respectively).

DESCRIPTION OF THE PREFERRED EMBODIMENTS

The present invention provides a novel steroid receptor kinase, Bin1, which is involved in the pathway for synthesis of the plant steroid hormone, brassinolide. Overexpression of Bin1 in transgenic plantsprovides plants characterized as having enhanced disease resistance, increased plant yield or vegetative biomass and increased seed yield. As used herein, the term "yield" or "increased plant yield" refers to increased plant biomass or seed yield relative to wild-type biomass.

BIN1 POLYPEPTIDES AND POLYNUCLEOTIDES

In a first embodiment, the present invention provides substantially pure Bin1 polypeptide. Bin1 polypeptide is exemplified by the amino acid sequence shown in FIG. 1 and SEQ ID NO:2. Bin1 polypeptide is characterized as having a predicted molecular weight of 130 kDa as determined by SDS-PAGE, and functioning in the brassinolide response pathway.

The term "substantially pure" as used herein refers to Bin1 polypeptide which is substantially free of other proteins, lipids, carbohydrates or other materials with which it is naturally associated. One skilled in the art can purify Bin1 using standard teclniques for protein purification. The substantially pure polypeptide will yield a single major band of about 130 kDa on a denaturing polyaciylamide gel. The purity of the Bin1 polypeptide can also be determined by amino-tenninal amino acid sequence analysis.

The invention includes functional Bin1 polypeptide as well as functional fragments thereof. As used herein, the term "functional polypeptide" refers to a polypeptide which possesses biological function or activity which is identified through a defined functional assay and which is associated with a particular biologic, morphologic, or phenotypic alteration in the cell. The tenn "functional fragments of Bin1 polypeptide", refers to all fragments of Bin1 that retain Bin1 activity, e.g., receptor protein kinase activity or the ability to bind brassinosteroids. Biologically functional fragments, for example, can vary in size from a polypeptide fragment as small as an epitope capable of binding an antibody molecule to a large polypeptide capable of participating in the characteristic induction or programming of phenotypic changes within a cell. An example of a functional fragment of Bin1 is a polypeptide including from about amino acid residue 588 to 649 of SEQ ID NO:2. This fragment includes the brassinosteroid binding domain of Bin1 polypeptide. Another functional fragment of Bin1 is a polypeptide including from about amino acid residue 831 to 1196 of SEQ ID NO:2. This fragment includes the protein kinase domain of Bin1 polypeptide.

The receptor protein kinase activity of Bin1 and the role of Bin1 in the brassinolide response pathway can be utilized in bioassays to identify biologically active fragments of Bin1 polypeptide or related polypeptides. For example, Bin1 may not only bind brassinosteroids, but other hormones as well, therefore an assay can be performed to detect Bin1 binding activity. In addition, inhibitors of Bin1 can be used to cause loss of Bin1 function resulting in, for example, male sterile plants, reduced stature, reduced yield, etc. Moreover, inhibition of Bin1 may be useful in horticulture for creating dwarf varieties.

Minor modifications of the Bin1 primary amino acid sequence may result in proteins which have substantially equivalent activity to the Bin1 polypeptide described herein in SEQ ID NO:2 (FIG. 1). Such modifications may be deliberate, as by site-directed mutagenesis, or may be spontaneous. All of the polypeptides produced by such Bin1 modifications are included herein as long as the peptide possesses Bin1 biological activity (i. e., receptor protein kinase activity). Further, deletion of one or more amino acids can also result in a modification of the structure of the resultant molecule without significantly altering its activity. Deletion can lead to the development of a smaller active molecule which could have broader utility. For example, it may be possible to remove amino or carboxy terminal amino acids required for Bin1 activity.

For example, a less active form of Bin1 has an amino acid change at residue 611 from glycine to glutamic acid. This mutant form has reduced affinity for the steroid. Other mutants can be produced which activate enzymatic activity. For example, a mutant can be produced such that the kinase domain is expressed, thereby allowing constitutive kinase activity.

Bin1 polypeptide includes amino acid sequences substantially the same as the sequence set forth in SEQ ID NO:2. The term "substantially the same" refers to amino acid sequences that retain the activity of Bin1 as described herein, e.g., receptor protein kinase activity. The Bin1 polypeptides of the invention include conservative variations of the polypeptide sequence. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

In another aspect, the invention provides isolated polynucleotides encoding Bin1 polypeptide having the amino acid sequence set forth in SEQ ID NO:2. The Bin1 gene has been mapped to a 5-kb interval on Arabidopsis chromosome 4. The Bin1 transcript contains a single, long open reading frame that encodes 1196 amino acid protein. The term "isolated" as used herein includes polynucleotides substantially free of other nucleic acids, proteins, lipids, carbohydrates or other materials with which it is naturally associated. Polynucleotide sequences of the invention include nucleic acid, cDNA and RNA sequences which encode Bin1. It is understood that polynucleotides encoding all or varying portions of Bin1 are included herein, as long as they encode a polypeptide with Bin1 activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription. Moreover, Bin1 polynucleotides of the invention include polynucleotides having alterations in the nucleic acid sequence which still encode functional Bin1. Alterations in Bin1 nucleic acid include but are not limited to intragenic mutations (e.g., point mutation, nonsense (stop), antisense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Invention polynucleotide sequences also include antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of Bin1 polypeptide encoded by such nucleotide sequences retains Bin1 receptor protein kinase activity. A "functional polynucleotide" denotes a polynucleotide which encodes a functional polypeptide as described herein. In addition, the invention also includes a polynucleotide encoding a polypeptide having the biological activity of the amino acid sequence set forth in SEQ ID NO:2 and having at least one epitope for an antibody immunoreactive with Bin1 polypeptide.

As used herein, the terms polynucleotides and nucleic acid sequences of the invention refer to nucleic acid, RNA and cDNA sequences.

Polynucleotides encoding Bin 1 include the nucleotide sequence set forth in FIG. 1 (SEQ ID NO:1), as well as nucleic acid sequences complementary to that sequence. Complementary sequences may include antisense polynucleotides. When the sequence is RNA, the deoxyribonucleotides A, G, C, and T of FIG. 1C are replaced by ribonucleotides A, G, C, and U, respectively. Also included in the invention are fragments ("probes") of the above-described nucleic acid sequences that are at least 15 bases in length, which is sufficient to permit the probe to selectively hybridize to nucleic acid that encodes the amino acid sequence set forth in FIG. 1 (SEQ ID NO:2). "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated Bin1 nucleotide sequences.

Specifically disclosed herein is a cDNA sequence for Bin1. FIG. 1 shows the complete cDNA and deduced protein sequences (SEQ ID NOs: 1 and 2, respectively). It is understood that homologs of the plant Bin1 are included herein and can be identified, for example, by using plant Bin1 nucleic acid probes based on SEQ ID NO:1.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. nucleic acid) of the hybridizing regions can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2 ×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. Optimal conditions will vary, depending on the particular hybridization reaction involved, and can be determined empirically.

Nucleic acid sequences of the invention can be obtained by several methods. For example, the nucleic acid can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned nucleic acid fragments with shared structural features; 3) polymerase chain reaction (PCR) on genomic nucleic acid or cDNA using primers capable of annealing to the nucleic acid sequence of interest; 4) computer searches of sequence databases for similar sequences; and 5) differential screening of a subtracted nucleic acid library.

Screening procedures which rely on nucleic acid hybridization make it possible to isolate any gene sequence from any organism, provided the appropriate probe is available. Oligonucleotide probes, which correspond to a part of the Bin1 sequence encoding the protein in question, can be synthesized chemically. This requires that short, oligopeptide stretches of the amino acid sequence must be known. The nucleic acid sequence encoding the protein can be deduced from the genetic code, however, the degeneracy of the code must be taken into account. It is possible to perform a mixed addition reaction when the sequence is degenerate. This includes a heterogeneous mixture of denatured double-stranded nucleic acid. For such screening, hybridization is preferably performed on either single-stranded nucleic acid or denatured double-stranded nucleic acid. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target nucleic acid to a single probe in the mixture which is its complete complement (Wallace, et al., *Nucl. Acid Res.*, 9:879, 1981). Alternatively, a subtractive library, as illustrated herein is useful for elimination of non-specific cDNA clones.

When the amino acid sequence is not known, the direct synthesis of nucleic acid sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In cases where significant portions of the amino acid sequence of a polypeptide are known, the production of labeled single or double-stranded nucleic acid or RNA probe sequences duplicating a sequence putatively present in the target cDNA may be employed in nucleic acid/nucleic acid hybridization procedures which are carried out on cloned copies of the cDNA which have been denatured into a single-stranded form (Jay, et al., *Nucl Acid Res.*, 11:2325, 1983).

A cDNA expression library, such as lambda gt11, can be screened indirectly for Bin1 peptides using antibodies specific for Bin1. Such antibodies can be either polyclonal or monoclonal and used to detect expression product indicative of the presence of Bin1 cDNA.

Detection of alterations in Bin1 nucleic acid (e.g., point mutation, nonsense (stop), missense, splice site and frameshift) and heterozygous or homozygous deletions can be effected by standard methods known to those of skill in the art including sequence analysis, Southern blot analysis, PCR based analyses (e.g., multiplex PCR, sequence tagged sites (STSs)) and in situ hybridization. Such proteins can be analyzed by standard SDS-PAGE and/or immunoprecipitation analysis and/or Western blot analysis, for example.

Nucleic acid sequences encoding Bin1 can be expressed in vitro by nucleic acid transfer into a suitable host cell. "Host cells" are cells in which a vector can be propagated and its nucleic acid expressed. The term "host cells" also includes any progeny or graft material, for example, of the parent host cell. It is understood that all progeny may not be identical to the parental cell since there may be mutations that occur during replication. However, such progeny are included when the term "host cell" is used. Methods of stable transfer, meaning that the foreign nucleic acid is continuously maintained in the host, are known in the art.

In the present invention, the Bin1 polynucleotide sequences may be inserted into a recombinant expression vector. The terms "recombinant expression vector" or "expression vector" refer to a plasmid, virus or other vehicle known in the art that has been manipulated by insertion or incorporation of the Bin1 genetic sequence. Such expression vectors contain a promoter sequence which facilitates the efficient transcription of the inserted Bin1 sequence. The expression vector typically contains an origin of replication, a promoter, as well as specific genes which allow phenotypic selection of the transformed cells.

Methods which are well known to those skilled in the art can be used to construct expression vectors containing the Bin1 coding sequence and appropriate transcriptional/ translational control signals. Such methods include in vitro recombinant nucleic acid techniques, synthetic techniques, and in vivo recombination/genetic techniques. (See, for example, the techniques described in Maniatis et al., 1989 Molecular Cloning A Laboratory Manual, Cold Spring Harbor Laboratory, N.Y.)

A variety of host-expression vector systems may be utilized to express the Bin1 coding sequence. These include but are not limited to microorganisms such as bacteria transformed with recombinant bacteriophage nucleic acid, plasmid nucleic acid or cosmid nucleic acid expression vectors containing the Bin1 coding sequence; yeast transformed with recombinant yeast expression vectors containing the Bin1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Bin1 coding sequence; insect cell systems infected with recombinant virus expression vectors (e.g., baculovirus) containing the Bin1 coding sequence; or animal cell systems infected with recombinant virus expression vectors (e.g., retroviruses, adenovirus, vaccinia virus) containing the Bin1 coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al, 1987, Methods in Enzymology 153:516–544). For example, when cloning in bacterial systems, inducible promoters such as pL of bacteriophage γ, plac, ptrp, ptac (ptrp-lac hybrid promoter) and the like may be used. When cloning in mammalian systems, promoters derived from the genome of mammalian cells (e.g., metallothionein promoter) or mammalian viruses (e.g., the retroviral long terminal repeat; adenovirus late promoter; the vaccinia virus 7.5K promoter) may be used. Promoters produced by recombinant nucleic acid or synthetic techniques may also be used to provide for transcription of the inserted Bin1 coding sequence.

In yeast, a number of vectors containing constitutive or inducible promoters may be used. For a review see, Current Protocols in Molecular Biology, Vol. 2, 1988, Ed. Ausubel et aL, Greene Publish. Assoc. & Wiley Interscience, Ch. 13; Grant et al., 1987, Expression and Secretion Vectors for Yeast, in Methods in Enzymology, Eds. Wu & Grossman, 31987, Acad. Press, N.Y., Vol. 153, pp.516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathem et aL, Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign nucleic acid sequences into the yeast chromosome.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and advantageously, plasma membrane insertion of the gene product may be used as host cells for the expression of Bin1.

Mammalian expression systems which utilize recombinant viruses or viral elements to direct expression may be engineered. For example, when using adenovirus expression vectors, the Bin1 coding sequence may be ligated to an adenovirus transcription/translation control complex, e.g., the late promoter and tripartite leader sequence. Alternatively, the vaccinia virus 7.5K promoter may be used. (e.g., see, Mackett el al., 1982, Proc. Natl. Acad. Sci. USA 79: 7415–7419; Mackett et al., 1984, J. Virol. 49: 857–864; Panicali et al., 1982, Proc. Natl. Acad. Sci. USA 79: 4927–4931). Of particular interest are vectors based on bovine papilloma virus which have the ability to replicate as extrachromosomal elements (Sarver, et al., 1981, Mol. Cell. Biol. 1: 486). Shortly after entry of this nucleic acid into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as, for example, the neo gene. Alternatively, the retroviral genome can be modified for use as a vector capable of introducing and directing the expression of the Bin1 gene in host cells (Cone & Mulligan, 1984, Proc. NatL Acad. Sci. USA 81:6349–6353). High level expression may also be achieved using inducible promoters, including, but not limited to, the metallothionein IIA promoter and heat shock promoters.

For long-term, high-yield production of recombinant proteins, stable expression is preferred. Rather than using expression vectors which contain viral origins of replication, host cells can be transformed with Bin1 cDNA controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign nucleic acid, engineered cells may be allowed to grow for 1–2 days in an enriched media, and then are switched to a selective media. A number of selection systems may be used, including, but not limited to the herpes simplex virus thymidine kinase gene (Wigler,et al., 1977, Cell 11: 223), hypoxanthine-guanine phosphoribosyltransferase gene (Szybalska & Szybalski, 1962, Proc. Natl. Acad. Sci. USA 48: 2026), and the adenine p-hosphoribosyltransferase (Lowy, et al., 1980, Cell 22: 817) genes can be employed in tk–, hgprt⁻ or aprt⁻ cells respectively. Additionally, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); the gpt gene, which confers resistance to mycophenolic acid (Mulligan & Berg, 1981, Proc. Natl. Acad. Sci. USA 78: 2072; the neo gene, which confers resistance to the aminoglycoside G-418 (Colberre-Garapin, et al., 1981, J. Mol. Biol. 150: 1); and the hygro gene, which confers resistance to hygromycin (Santerre, et al., 1984, Gene 30: 147) genes. Recently, additional selectable genes have been described, namely trpB, which allows cells to utilize indole in place of tiyptophan; hisD, which allows cells to utilize histinol in place of histidine (Hartman & Mulligan, 1988, Proc. Natl Acad. Sci. USA 85: 8047); and ODC (ornithine decarboxylase) which confers resistance to the ornithine decarboxylase inhibitor, 2-(difluoromethyl)-DL-omithine, DFMO (McConlogue L., 1987, In: Current Communications in Molecular Biology, Cold Spring Harbor Laboratory ed.).

When the host is a eukaryote, transfection of nucleic acid may be accomplished by employing as calcium phosphate co-precipitates and conventional mechanical procedures such as microinjection, electroporation, insertion of a plasmid encased in liposomes, or virus vectors. Eukaryotic cells can also be cotransforned with nucleic acid sequences encoding a Bin1 polypeptide of the invention, and a second foreign nucleic acid molecule encoding a selectable phenotype. Another method employs a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of recombinantly expressed polypeptides, or fragments thereof, provided by the invention, may be carried out by conventional means including preparative chromatography and immunological separations involving monoclonal or polyclonal antibodies.

BIN1 ANTIBODIES

The invention also includes antibodies immunoreactive with Bin1 polypeptide or antigenic fragments thereof. Antibodies of the invention are useful for modulating Bin1 ligand binding, for example. Antibodies directed against peptides derived from the extracellular domain of Bin1 are preferred (e.g., peptides contained in the domain from about amino acid 588 to 649 of SEQ ID NO:2). Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature*, 256:495, 1975).

The preparation of polyclonal antibodies is well-known to those skilled in the art. See, for example, Green et al., Production of Polyclonal Antisera, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992), which are hereby incorporated by reference.

The preparation of monoclonal antibodies likewise is conventional. See, for example, Kohler & Milstein, *Nature* 256:495 (1975); Coligan et al., sections 2.5.1–2.6.7; and Harlow et al., ANTIBODIES: A LABORATORY MANUAL, page 726 (Cold Spring Harbor Pub. 1988), which are hereby incorporated by reference. Briefly, monoclonal antibodies can be obtained by injecting mice with a composition comprising an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., *Purification of Immunoglobulin G (IgG)*, in METHODS IN MOLECULAR BIOLOGY, VOL. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. With increasing evidence that steroids affect the cell surface and alter ion permeability, as well as the release of neurohormones and neurotransmitters, antibodies to extracellular receptors such as Bin1 may have therapeutic applications. Antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., *Int. J. Cancer* 46:310 (1990), which are hereby incorporated by reference.

Alternatively, a therapeutically useful anti-Bin1 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989), which is hereby incorporated in its entirety by reference. Techniques for producing humanized monoclonal antibodies are described, for example, by Jones et al., *Nature* 321: 522 (1986); Riechmann et al., *Nature* 332: 323 (1988); Verhoeyen et al., *Science* 239: 1534 (1988); Carter et al., *Proc. Nat'l Acad. Sci. USA* 89: 4285 (1992); Sandhu, *Crit. Rev. Biotech.* 12: 437 (1992); and Singer et al., *J. Immunol.* 150: 2844 (1993), which are hereby incorporated by reference.

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., *Ann. Rev. Immunol.* 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described by Green et al., *Nature Genet.* 7:13 (1994); Lonberg et al., *Nature* 368:856 (1994); and Taylor et al., *Int. Immunol.* 6:579 (1994), which are hereby incorporated by reference.

Antibody fragments of the present invention can be prepared by proteolytic hydrolysis of the antibody or by expression in *E. coli* of nucleic acid encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and No. 4,331,647, and references contained therein. These patents are hereby incorporated in their entireties by reference. See also Nisoiihoff et al., *Arch. Biochem. Biophys.* 89:230 (1960); Porter, *Biochem. J.* 73:119 (1959); Edelman etal, METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., *Proc. Nat'l Acad. Sci. USA* 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising nucleic acid sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird etal., *Science* 242:423–426 (1988); Ladneret al., U.S. Pat. No. 4,946,778; Pack et al., *Bio/Technology* 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The term "antibody" as used in this invention includes intact molecules as well as fragments thereof, such as Fab, F(ab')2, and Fv which are capable of binding to an epitopic determinant present in Bin1 polypeptide. Such antibody fragments retain some ability to selectively bind with its antigen or receptor.

As used in this invention, the term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the Bin1 polypeptide of the invention can be prepared using an intact polypeptide or fragments containing small peptides of interest as the immunizing antigen. For example, it may be desirable to produce antibodies that specifically bind to the N- or C-terminal domains of Bin1. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Invention polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

It is also possible to use the anti-idiotype technology to produce invention monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

GENETICALLY MODIFIED PLANTS AND METHODS OF MAKING

In another embodiment, the invention provides a method for producing a genetically modified plant characterized as having increased yield as compared to a plant which has not been genetically modified (e.g., a wild-type plant). The term "yield" has been previously defined herein. The invention method comprises the steps of introducing at least one nucleic acid sequence encoding Bin1, into a plant cell to obtain a transformed plant cell wherein the nucleic acid sequence is operably associated with a promoter, producing a plant from the transformed plant cell under conditions which allow expression of Bin1 polypeptide; and thereafter selecting a plant exhibiting increased yield.

The term "genetic modification" as used herein refers to the introduction of one or more heterologous nucleic acid sequences into one or more plant cells, to provide sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, potatoes, grapes, strawberries, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, oak, etc.

The term "heterologous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In the broad method of the invention, at least one nucleic acid sequence encoding Bin1 polypeptide is associated to a suitable promoter. It may be desirable to introduce more than one copy of Bin1 polynucleotide into a plant for enhanced Bin1 expression. For example, multiple copies of the gene would have the effect of increasing production of Bin1 polypeptide in the plant allowing for greater brassinosteroid or other steroid/hormone action.

Genetically modified plants of the present invention are produced by introducing into a plant cell, a vector including at least one nucleic acid sequence encoding Bin1. To be effective once introduced into plant cells, the Bin1 nucleic acid sequence must be operably associated with a promoter which is effective in the plant cells to cause transcription of Bin1. Additionally, a polyadenylation sequence or transcription control sequence, also recognized in plant cells may also be employed. It is preferred that the vector harboring the nucleic acid sequence to be inserted also contain one or more selectable marker genes so that the transformed cells can be selected from non-transformed cells in culture, as described herein.

The term "operably associated" refers to a functional linkage between a promoter sequence and the Bin1 nucleic acid sequence regulated by the promoter. The operably linked promoter controls the expression of the Bin1 nucleic acid sequence.

The expression of Bin1 polynucleotides in the present invention may be driven by a number of promoters. Although the endogenous, or native promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al., *Nature*, 310:511, 1984; Odell, et al., *Nature*, 313:810, 1985); the full-length transcript promoter from Figwort Mosaic Virs (FMV) (Gowda, et al., *J Cell Biochem.*, 13D: 301, 1989) and the coat protein promoter to TMV (Takamatsu, et al., *EMBO J*. 6:307, 1987). Alternatively, plant promoters such as the light-inducible promoter from the small subunit of ribulose bis-phosphate carboxylase (ssRUBISCO) (Coruzzi, et al., *EMBO J*, 3:1671, 1984; Broglie, etal., *Science*, 224:838, 1984); man- nopine synthase promoter (Velten, et al., *EMBO J*, 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley, et al., *Mol. Cell. Biol*, 6:559, 1986; Severin, et al., *Plant Mol. Biol.*, 15:827, 1990) may be used.

Promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., *Proc. Natl. Acad. Sci., U.S.A.*, 90:4567, 1993); In2-1 and In2-2 regulator sequences which are activated by substituted benzenesulfonamides, e.g., herbicide safeners (Hershey, et al., *Plant Mol. Biol.*, 17:679, 1991); and the GRE regulatory sequences which are induced by glucocorticoids (Schena, et al., *Proc. Natl. Acad. Sci., U.S.A.*, 88:10421, 1991). Other promoters, both constitutive and inducible will be known to those of skill in the art.

The particular promoter selected should be capable of causing sufficient expression to result in the production of an effective amount of structural gene product, e.g., Bin1 polypeptide to cause increased plant biomass, and therefore increased yield. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova, et al., *Plant J.*, 2:291, 1992). Other tissue specific promoters useful in transgenic plants, including the cdc2a promoter and cyc07 promoter, will be known to those of skill in the art. (See for example, Ito, et al., *Plant Mol. Biol.*, 24:863, 1994; Martinez, et al., *Proc. Natl. Acad. Sci. USA*, 89:7360, 1992; Medford, et al., *Plant Cell*, 3:359, 1991; Terada, et al., *Plant Journal*, 3:241, 1993; Wissenbach, et al, *Plant Journal*, 4:411, 1993).

There are promoters known which limit expression to particular plant parts or in response to particular stimuli. For example, potato tuber specific promoters, such as the patatin promoters or the promoters for the large or small subunits of ADPglucose pyrophosphorylase, could be operably associated with Bin1 to provide expression primarily in the tuber and thus, provide resistance to attacks on the tuber, such as by Erwinia. A fruit specific promoter would be desirable to impart resistance to Botrytis in strawberries or grapes. A root specific promoter would be desirable to obtain expression of Bin1 in wheat or barley roots to provide resistance to Ggt. One skilled in the art will know of many such plant part-specific promoters which would be useful in the present invention.

Alternatively, the promoters utilized may be selected to confer specific expression of Bin1 in response to fungal infection. The infection of plants by fungal pathogens activate defense-related or pathogenesis-related (PR) genes which encode (1) enzymes involved in phenylpropanoid metabolism such as phenylalanine ammonia lyase, chalcone synthase, 4-coumarate coA ligase and coumaric acid 4-hydroxylase, (2) proteins that modify plant cell walls such as hydroxyproline-rich glycoproteins, glycine-rich proteins, and peroxidases, (3) enzymes, such as chitinases and glucanases, that degrade the fungal cell wall, (4) thaumatin-like proteins, or (5) proteins of as yet unknown function. The defense-related or PR genes have been isolated and characterized from a number of plant species. The promoters of these genes may be used to obtain expression of Bin1 in transgenic plants when such plants are challenged with a pathogen, particularly a fungal pathogen such as Pi. The particular promoter selected should be capable of causing sufficient expression of Bin1 to result in the production of an effective amount of polypeptide.

Promoters used in the nucleic acid constructs of the present invention may be modified, if desired, to affect their control characteristics. For example, the CaMV 35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV 35S" promoter thus includes variations of CaMV 35S promoter, e.g., promoters derived by means of ligation with operator regions, random or controlled mutagenesis, etc. Furthermore, the promoters may be altered to contain multiple "enhancer sequences" to assist in elevating gene expression.

Optionally, a selectable marker may be associated with the nucleic acid sequence to be inserted. As used herein, the term "marker" refers to a gene encoding a trait or a phenotype which permits the selection of, or screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase and amino-glycoside 3'-O-phospho-transferase II (kanamycin, neomycin and G418 resistance). Other suitable markers will be known to those of skill in the art.

Vector(s) employed in the present invention for transformation of plant cells comprise a nucleic acid sequence encoding Bin1 polypeptide, operably associated with a promoter. To effect a transformation process in accordance with the present invention, it is first necessary to construct a suitable vector and properly introduce it into the plant cell. Details of the construction of vectors utilized herein are known to those skilled in the art of plant genetic engineering.

Bin1 nucleic acid sequences utilized in the present invention can be introduced into plant cells using Ti plasmids of *Agrobacterium tumefaciens*, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al, *Science*, 227:1229, 1985, both incorporated herein by reference). In addition to plant transformation vectors derived from the Ti or root-inducing (Ri) plasmids of Agrobacterium, alternative methods of transformation may be utilized including the use of liposomes, electroporation, chemicals that increase free nucleic acid uptake, transformation using viruses or pollen and the use of biolistic transformation.

One of skill in the art will be able to select an appropriate vector for introducing the Bin1 polynucleotide sequence in a relatively intact state. Thus, any vector which will produce a plant carrying the introduced nucleic acid sequence should be sufficient. Even use of a naked piece of nucleic acid would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of Bin1 nucleic acid sequence.

For example, a Bin1 nucleic acid sequence can be introduced into a plant cell utilizing *Agrobacterium tumefaciens* containing the Ti plasmid, as mentioned briefly above. In using an A. tumefaciens culture as a transformation vehicle, it is advantageous to use a non-oncogenic strain of Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer nucleic acid (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology,* 1:262, 1983; Hoekema, et al., *Nature*, 303:179, 1983). Such a binary system is preferred because it does not require integration into the Ti plasmid of Agrobacteriurn, which is an older methodology.

Methods involving the use of Agrobacterium in transformation according to the present invention include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in planta transformation by Agrobacterium, as described by Bechtold, et al., (C. R. *Acad. Sci. Paris*, 316:1194, 1993) and exemplified in the Examples herein. This approach is based on the vacuum infiltration or dipping of a suspension of Agrobacterium cells.

The preferred method of introducing Bin1 polynucleotide into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, Bin1 polynucleotide can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

Bin1 polynucleotide can also be introduced into plant cells by electroporation (Fromm, et al., *Proc. Natl. Aicad. Sci., U.S.A.*, 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing Bin1 polynucleotide into a plant cell is high velocity ballistic penetration by small particles with the nucleic acid to be introduced contained either within the matrix of such particles, or on the surface thereof (Klein, et al., *Nature* 327:70, 1987). Bombardment transformation methods are also described in Sanford, et al. (*Techniques* 3:3–16, 1991) and Klein, et al. (*Bio/Techniques* 10:286, 1992). Although, typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral nucleic acid genome is inserted into a parent bacterial plasmid creating a recombinant nucleic acid molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing Bin1 into the plant cell, including chemical and physical means as described above. Preferably, contacting refers to introducing the nucleic acid or vector into plant cells (including an explant, a meristem or a seed), via *Agrobacterium tumefaciens* transformed with the Bin1 encoding nucleic acid as described above.

Normally, a transformed plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species, but generally the process is initiated by first providing a suspension of protoplasts. In certain species, plant formation can be induced from the protoplast suspension, followed by ripening and germination as natural plant. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, the genotype, and the history of the culture. If these variables are controlled, regeneration is reproducible.

Regeneration also occurs from plant callus, explants, organs or parts. Transformation can be performed in the context of organ or plant part regeneration. (see *Methods in Enzymology*, Vol. 118 and Klee, et al., *Annual Review of Plant Physiology*, 38:467, 1987). Utilizing the leaf disk-transformation-regeneration method of Horsch, et al., *Science*, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants is self crossed to produce a homozygous inbred plant. The resulting inbred plant produces seed containing the newly introduced foreign gene(s). These seeds can be grown to produce plants that would produce the selected phenotype, e.g. increased yield.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting increased yield or biomass as compared with wild-type plants can be selected by visual observation. The invention includes plants produced by the method of the invention, as well as plant tissue and seeds.

In yet another embodiment, the invention provides a method for producing a genetically modified plant characterized as having increased yield as compared with a wild-type plant. The method includes introducing at least one nucleic acid sequence encoding Bin1 polypeptide into a plant cell to obtain a transformed plant cell; growing the transformed plant cell under conditions which allow expression of Bin1 polypeptide to obtain a plant having increased yield. Conditions such as environmental and promoter inducing conditions vary from species to species, but should be the same within a species.

In another embodiment, the invention provides a method of producing a plant characterized as having increased yield by contacting a susceptible plant with a Bin1 promoter-inducing amount of an agent which induces Bin1 gene expression, wherein induction of Bin1 gene expression results in production of a plant having increased yield as compared to a plant not contacted with the agent.

A "susceptible plant" refers to a plant that can be induced to utilize its endogenous Bin1 gene to achieve increased yield. The term "promoter inducing amount" refers to that amount of agent necessary to elevate Bin1 gene expression above Bin1 expression in a plant cell not contacted with the agent. For example, a transcription factor or a chemical agent may be used to elevate gene expression from Bin1 native promoter. Alternatively, Bin1 promoter may be a heterologous promoter susceptible to induction. The invention method envisions contacting cells containing endogeous Bin1 promoter or recombinantly produced Bin1 promoter.

PATHOGEN RESISTANT PLANTS

In another aspect of the invention, it is envisioned that increased expression of Bin1 in a plant cell or in a plant, increases resistance of that cell/plant to plant pests or plant pathogens. For example, field studies have shown that brassinolides are effective as pesticides, therefore, increased expression of Bin1 would result in increased amounts of brassinosteroid receptor in the plant. In addition, increased Bin1 expression may also cause increased resistance to pesticides (safeners). Bin1 therefore, protects plants against pests as well as against pesticides.

In yet another embodiment, the invention provides a method of producing genetically transformed, disease resistant plants, comprising introducing into the genome of a plant cell to obtain a transformed plant cell, a nucleic acid construct comprising (i) a promoter which functions in plant cells to cause the production of an RNA sequence; and (ii)

a nucleic acid sequence encoding Bin1 polypeptide; and regenerating from the transformed plant cell genetically transformed plants which express Bin1 polypeptide in an amount effective to inhibit infection by a bacterial or fungal pathogen. The invention includes plants, seeds, etc., produced by the method of the invention.

As used herein, the term "pathogen-resistance" is used to indicate causing a reduction in damage to a plant or a crop due to infection by a bacterial or fungal pathogen. The method of the invention is useful for inhibiting the growth of the agronomically important fungal pathogens, including, Verticillium dahliae, one of the most widespread and damaging plant pathogens, causing disease in many plants, Phytophthora infestans (Pi), the causal pathogen of late blight disease in potato and tomato, Botrytis cinerea (Bc), the source of gray mold on various fruits and vegetables, Septoria nodorum (Sn), the causal agent of wheat glume blotch, Pseudocercosporella herpotrichoides (Ph), the causal agent of wheat eyespot, and Gaeumannomyces graminis var tritici (Ggt), the causal agent of Take-all disease in cereals and Erwinia carotovora, the causal agent of potato soft rot, a post-harvest disease of potatoes.

TRANSGENIC ANIMALS

In another embodiment, the present invention relates to transgenic animals having cells that express a homologue of plant Bin1. While not wanting to be bound by a particular theory, it is believed that a mammalian homologue of Bin1 polypeptide of the invention, would bind to mammalian steroids. Other homologues of Bin1 polypeptide and polynucleotide of the invention are also included herein. Such transgenic animals represent a model system for the study of steroid-receptor interaction and binding to develop more effective therapeutics.

The term "animal" here denotes all mammalian species except human. It also includes an individual animal in all stages of development, including embryonic and fetal stages. Farm animals (pigs, goats, sheep, cows, horses, rabbits and the like), rodents (such as mice), and domestic pets (for example, cats and dogs) are included within the scope of the present invention.

A "transgenic" animal is any animal containing cells that bear genetic information received, directly or indirectly, by deliberate genetic manipulation at the subcellular level, such as by microinjection or infection with recombinant virus. "Transgenic" in the present context does not encompass classical crossbreeding or in vitro fertilization, but rather denotes animals in which one or more cells receive a recombinant nucleic acid molecule. Although it is highly preferred that this molecule be integrated within the animal's chromosomes, the present invention also contemplates the use of extrachromosomally replicating nucleic acid sequences, such as might be engineered into yeast artificial chromosomes.

The term "transgenic animal" also includes a "germ cell line" transgenic animal. A germ cell line transgenic animal is a transgenic animal in which the genetic information has been taken up and incorporated into a germ line cell, therefore conferring the ability to transfer the information to offspring. If such offspring in fact possess some or all of that information, then they, too, are transgenic animals.

The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

The transgene to be used in the practice of the subject invention is a nucleic acid sequence encoding Bin1 or a nucleic acid sequence comprising a modified Bin1 coding sequence. In one embodiment, Bin1 encoding nucleic acid is the transgene, resulting in cells which express Bin1. Bin1 can either be the native, wild-type sequence, such as a homologue set forth in SEQ ID NO:1, or a modified sequence, such as a mutant having a G611Q alteration.

In another embodiment, the mammalian Bin1 homologue gene is disrupted by homologous targeting in embryonic stem cells. For example, the entire mature N-terminal region of the Bin1 gene may be deleted, resulting in expression of a truncated receptor. Optionally, the Bin1 disruption or deletion may be accompanied by insertion of or replacement with other nucleic acid sequences, such as a non-functional Bin1 sequence. In yet other embodiments, the transgene comprises nucleic acid antisense to the coding sequence for Bin1. In another embodiment, the transgene comprises nucleic acid encoding an antibody or receptor peptide sequence which is able to bind to Bin1. Where appropriate, nucleic acid sequences that encode proteins having Bin1 activity but differ in nucleic acid sequence due to the degeneracy of the genetic code may also be used herein, as may truncated forms, allelic variants and interspecies homologues.

VARIANTS OF Bin1

The term "Bin1 variant" as used herein means a molecule that simulates at least part of the structure of Bin1 and binds brassinosteroids. Homologues of Bin1 variants may also be useful in preventing steroid binding, thereby preventing oocyte maturation, for example, or maintaining a plant in a vegetative state, as compared to the senescent state.

In one embodiment, the present invention relates to peptides and peptide derivatives that have fewer amino acid residues than Bin1 and retain the ability to bind brassinosteroids. Such peptides and peptide derivatives could represent research and diagnostic tools useful in the study of steroid binding and the development of more effective therapeutics and contraceptives. Fragments of Bin1 according to the invention include those which correspond to the regions of Bin1 that are proposed to bind to brassinosteroids, e.g., amino acid residues 588 to 649 of SEQ ID NO:2, which are exposed on the cell surface.

Bin1 can be altered by changing the nucleic acid encoding the protein. Preferably, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Variants useful for the present invention comprise analogs, homologs, muteins and mimetics of Bin1 that retain protein kinase activity. Peptides of the Bin1 refer to portions of the amino acid sequence of Bin1 that also retain this ability. The variants can be generated directly from Bin1 itself by chemical modification, by proteolytic enzyme digestion, or by combinations thereof. Additionally, genetic engineering techniques, as well as methods of synthesizing polypeptides directly from amino acid residues, can be employed.

Peptides of the invention can be produced by standard recombinant methods or synthesized by such commonly used methods as t-BOC or FMOC protection of alpha-amino groups. Both of these latter methods involve stepwise syntheses whereby a single amino acid is added at each step starting from the C terminus of the peptide (See, Coligan, et al, *Current Protocols in Immunology*, Wiley Interscience, 1991, Unit 9).

Peptides of the invention can also be synthesized by the well known solid phase peptide synthesis methods described Merrifield, *J. Am. Chem. Soc.*, 85:2149, 1962), and Stewart and Young, *Solid Phase Peptides Synthesis*, (Freeman, San Francisco, 1969, pp.27–62), using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

The term "substantially purified" as used herein refers to a molecule, such as a peptide that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. One skilled in the art can purify Bin1 peptides using standard protein purification methods and the purity of the polypeptides can be determined using standard methods including, e.g., polyacrylamide gel electrophoresis (e.g., SDS-PAGE), column chromatography (e.g, high performance liquid chromatography (HPLC)), and amino-terminal amino acid sequence analysis.

Non-peptide compounds that mimic the binding and function of Bin1 ("mimetics") can be produced by the approach outlined in Saragovi et al., *Science* 253: 792–95 (1991). Mimetics are molecules which mimic elements of protein secondary structure. See, for example, Johnson et al., "Peptide Turn Mimetics," in BIOTECHNOLOGY AND PHARMACY, Pezzuto et aL, Eds., (Chapman and Hall, New York 1993). The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of Bin1 itself.

Longer peptides can be produced by the "native chemical" ligation technique which links together peptides (Dawson, et al., *Science*, 266:776, 1994). Variants can be created by recombinant techniques employing genomic or cDNA cloning methods. Site-specific and region-directed mutagenesis techniques can be employed. See CURRENT PROTOCOLS IN MOLECULAR BIOLOGY vol. 1, ch. 8 (Ausubel et al. eds., J. Wiley & Sons 1989 & Supp. 1990–93); PROTEIN ENGINEERING (Oxender & Fox eds., A. Liss, Inc. 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit., and CURRENT PROTOCOLS IN MOLECULAR BIOLOGY, vols. 1 & 2, supra.

Bin1-BINDING AND BLOCKING AGENTS

In yet another embodiment, the present invention relates to Bin1-binding agents that block brassinosteroid binding to Bin1 receptor polypeptide. Further, binding or blocking agents may be useful for Bin1 receptor homologues in the mammalian system. Such agents could represent research and diagnostic tools in the study of steroid binding and cellular responses as well as the development of more effective therapeutics. Steroids have recently been shown to have effects on neurosecretion and Ca2+entry or mobilization in the cell (McEwen, B., TIPS, Elsevier Science Publishers Ltd. (UK), 1991, Vol. 12, pp141–147). Bin1-binding or blocking agents are also effective for maintaining a plant in a vegetative state for example. Deficiency of Bin1 receptor may also be associated with male infertility, therefore, blocking brassinosteroid binding to Bin1 may be a useful contraceptive regime. Further, the inhibition of Bin1 may be associated with inhibition of oocyte maturation.

In the context of brassinosteroid binding to Bin1, the phrase "Bin1-binding agent" denotes a naturally occurring ligand of Bin1 such as, for example, a brassinosteroid or other hormone, a synthetic ligand of Bin1, or appropriate derivatives of the natural or synthetic ligands, as well as small molecules. The determination and isolation of ligands is well described in the art. See, e.g., Lerner, *Trends NeuroSci.* 17:142–146 (1994) which is hereby incorporated in its entirety by reference. A Bin1-binding agent that blocks brassinosteroid binding to Bin-1 is suitable according to the invention for maintaining plants in a longer-lived vegetative state, for example.

SCREEN FOR BIN1 BINDING AND BLOCKING AGENTS

In another embodiment, the invention provides a method for identifying a binding or blocking agent, which binds to Bin1 or blocks steroid binding to Bin1 polypeptide. The method includes incubating components comprising the agent and Bin1 polypeptide under conditions sufficient to allow the components to interact to form polypeptide/agent complex and detecting the presence of peptide bound agent by size separation, physical separation, or other standard methods. Agents that bind to Bin1 include peptides, peptidomimetics, polypeptides, chemical compounds, small molecules and biological agents as described above. In addition to inhibition of brassinosteroid binding, one of skill in the art could screen for inhibition of Bin1 binding to a hormone to determine if a compound or agent was a Bin1 polypeptide binding or blocking agent.

Incubation includes conditions which allow contact between the agent and Bin1 polypeptide. Contacting includes in solution and in solid phase. The test agent may optionally be a combinatorial library that permits screening a plurality of agents. Agents identified in the method of the invention can be further evaluated, detected, cloned, sequenced, and the like, either in solution or after binding to a solid support, by any method usually applied to the detection of a small molecule or a specific nucleic acid sequence. Nucleic acid sequences can be analyzed by commonly used techniques such as PCR, oligomer restriction (Saiki, et al., *Bio/Technology*, 3:1008–1012, 1985), allele-specific oligonucleotide (ASO) probe analysis (Conner, et al., *Proc. Natl Acad. Sci. USA*, 80:278, 1983), oligonucleotide ligation assays (OLAs) (Landegren, et al., *Science*, 241:1077, 1988), and the like. Molecular techniques for nucleic acid analysis have been reviewed (Landegren, et al., *Science*, 242:229–237, 1988).

To determine if an agent can functionally complex with the Bin1 polypeptide, the agent is incubated and any complex formed between Bin1 and the agent is separated from unbound Bin1 polypeptide. The agent can then be isolated from the Bin1 complex.

Also included in the screening method of the invention are combinatorial chemistry methods for identifying chemical compounds that bind to Bin1. Ligands/agents that bind to Bin1 can be assayed in standard labelling assays. Screening methods include inhibition of brassinosteroid or hormone binding to Bin1 (e.g., use radiolabeled brassinosteroid). Thus, the screening method is also useful for identifying variants, binding or blocking agents, etc., which functionally, if not physically (e.g., sterically) act as antagonists or agonists, as desired.

Ligands or test agents can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the test agent, or will be able to ascertain such, using routine experimentation.

Further, commonly used binding assays, such as an equilibrium saturation binding assay can be utilized to identify Bin1 binding and blocking agents.

ANTISENSE or RIBOZYME INHIBITION OF Bin1

Antisense technology offers a very specific and potent means of providing plants that can be maintained in vegetative state, thereby increasing biomass or seed yield. Antisense molecules are introduced into cells that contain Bin1, for example, and function by decreasing the amount of Bin1 expression in a cell. Antisense polynucleotides in context of the present invention includes both short sequences of nucleic acid known as oligonucleotides of usually 10–50 bases in length as well as longer sequences of nucleic acid that may exceed the length of the Bin1 gene sequence itself. Antisense polynucleotides useful for the present invention are complementary to specific regions of a corresponding target mRNA. Hybridization of antisense polynucleotides to their target transcripts can be highly specific as a result of complementary base pairing. The capability of antisense polynucleotides to hybridize is affected by such parameters as length, chemical modification and secondary structure of the transcript which can influence polynucleotide access to the target site. See Stein et al, *Cancer Research* 48:2659 (1988). An antisense polynucleotide can be introduced to a cell by introducing a nucleic acid segment that codes for the polynucleotide. An antisense polynucleotide can also be introduced to a cell by adding the polynucleotide to the environment of the cell such that the cell can take up the polynucleotide directly. The latter route is preferred for the shorter polynucleotides of up to about 20 bases in length.

In selecting the preferred length for a given polynucleotide, a balance must be struck to gain the most favorable characteristics. Shorter polynucleotides such as 10-to 15-mers, while offering higher cell penetration, have lower gene specificity. In contrast, while longer polynucleotides of 20–30 bases offer better specificity, they show decreased uptake kinetics into cells. See Stein et al., PHOSPHOROTHIOATE OLIGODEOXYNUCLEOTIDE ANALOGUES in "Oligodeoxynucleotides—Antisense Inhibitors of Gene Expression" Cohen, ed. McMillan Press, London (1988). Accessibility to mRNA target sequences also is of importance and, therefore, loop-forming regions in targeted mRNAs offer promising targets. In this disclosure the term "polynucleotide" encompasses both oligomeric nucleic acid moieties of the type found in nature, such as the deoxyribonucleotide and ribonucleotide structures of nucleic acid and RNA, and man-made analogues which are capable of binding to nucleic acids found in nature. The polynucleotides of the present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind to naturally occurring nucleic acid and RNA structures. Such polynucleotides may be prepared by methods well-known in the art, for instance using commercially available machines and reagents available from Perkin-Elmer/Applied Biosystems (Foster City, Calif.).

Phosphodiester-linked polynucleotides are particularly susceptible to the action of nucleases in serum or inside cells, and therefore in a preferred embodiment the polynucleotides of the present invention are phosphorothioate or methyl phosphonate-linked analogues, which have been shown to be nuclease-resistant. Persons of ordinary skill in this art will be able to select other linkages for use in the invention. These modifications also may be designed to improve the cellular uptake and stability of the polynucleotides.

The polynucleotides which have the capability to hybridize with mRNA targets can inhibit expression of corresponding gene products by multiple mechanisms. In "translation arrest," the interaction of polynucleotides with target mRNA blocks the action of the ribosomal complex and, hence, prevents translation of the messenger RNA into protein. Haeuptle et al., *Nucl. Acids. Res.* 14:1427 (1986). In the case of phosphodiester or phosphorothioate nucleic acid polynucleotides, intracellular RNase H can digest the targeted RNA sequence once it has hybridized to the nucleic acid oligomer. Walder and Walder, *Proc. Natl. Acad Sci. USA* 85:5011 (1988). As a further mechanism of action, in "transcription arrest" it appears that some polynucleotides can form "triplex," or triple-helical structures with double stranded genomic nucleic acid containing the gene of interest, thus interfering with transcription by RNA polymerase. Giovannangeli et al., *Proc. Natl. Acad. Sci.* 90:10013 (1993); Ebbinghaus et al. *J. Clin. Invest.* 92:2433 (1993).

In one preferred embodiment, Bin1 polynucleotides are synthesized according to standard methodology. Phosphorothioate modified nucleic acid polynucleotides typically are synthesized on automated nucleic acid synthesizers available from a variety of manufacturers. These instruments are capable of synthesizing nanomole amounts of polynucleotides as long as 100 nucleotides. Shorter polynucleotides synthesized by modern instruments are often suitable for use without further purification. If necessary, polynucleotides may be purified by polyacrylamide gel electrophoresis or reverse phase chromatography. See Sambrook et al., MOLECULAR CLONING: A Laboratory Manual, Vol. 2, Chapter 11, Cold Spring Harbor Laboratory Press, Cold Spring Harbor, N.Y. (1989).

Alternatively, a Bin1 polynucleotide in the form of antisense RNA may be introduced to a cell by its expression within the cell from a standard nucleic acid expression vector. Bin1 nucleic acid antisense sequences can be cloned from standard plasmids into expression vectors, which expression vectors have characteristics permitting higher levels of, or more efficient expression of the resident polynucleotides. At a minimum, these constructs require a prokaryotic or eukaryotic promoter sequence which initiates transcription of the inserted nucleic acid sequences. A preferred expression vector is one where the expression is inducible to high levels. This is accomplished by the addition of a regulatory region which provides increased transcription of downstream sequences in the appropriate host cell. See Sambrook et al., Vol. 3, Chapter 16 (1989).

For example, Bin1 antisense expression vectors can be constructed using the polymerase chain reaction (PCR) to amplify appropriate fragments from single-stranded cDNA of a plasmid such as pRc in which Bin1 cDNA has been incorporated. Fang et al., *J. Biol. Chem.* 267: 25889–25897 (1992). Polynucleotide synthesis and purification techniques are described in Sambrook et al. and Ausubel et al. (eds.), CURRENT PROTOCOLS IN MOLECULAR BIOLOGY (Wiley Interscience 1987) (hereafter "Ausubel"), respectively. The PCR procedure is performed via well-known methodology. See, for example, Ausubel, and Bangham, "The Polymerase Chain Reaction: Getting Started," in PROTOCOLS IN HUMAN MOLECULAR GENETICS (Humana Press 1991). Moreover, PCR kits can be purchased from companies such as Stratagene Cloning Systems (La Jolla, Calif.) and Invitrogen (San Diego, Calif.).

The products of PCR are subcloned into cloning vectors. In this context, a "cloning vector" is a nucleic acid molecule, such as a plasmid, cosmid or bacteriophage, that can replicate autonomously in a host prokaryotic cell. Cloning vectors typically contain one or a small number of restriction endonuclease recognition sites at which foreign nucleic acid sequences can be inserted in a determinable fashion without loss of an essential biological function of the vector, as well as a marker gene that is suitable for use in the identification and selection of cells transformed with the cloning vector. Suitable cloning vectors are described by Sambrook et al., Ausubel, and Brown (ed.), MOLECULAR BIOLOGY LABFAX (Academic Press 1991). Cloning vectors can be obtained, for example, from GIBCO/BRL (Gaithersburg, Md.), Clontech Laboratories, Inc. (Palo Alto, Calif.), Promega Corporation (Madison, Wis.), Stratagene Cloning Systems (La Jolla, Calif.), Invitrogen (San Diego, Calif.), and the American Type Culture Collection (Rockville, Md.).

Preferably, the PCR products are ligated into a "TA" cloning vector. Methods for generating PCR products with a thymidine or adenine overhang are well-known to those of skill in the alt. See, for example, Ausubel at pages 15.7.1–15.7.6. Moreover, kits for performing TA cloning can be purchased from companies such as Invitrogen (San Diego, Calif.).

Cloned antisense fragments are amplified by transforming competent bacterial cells with a cloning vector and growing the bacterial host cells in the presence of the appropriate antibiotic. See, for example, Sambrook et al., and Ausubel. PCR is then used to screen bacterial host cells for Bin1 antisense orientation clones. The use of PCR for bacterial host cells is described, for example, by Hofmann et al., "Sequencing DNA Amplified Directly from a Bacterial Colony," in PCR PROTOCOLS: METHODS AND APPLICATIONS, White (ed.), pages 205–210 (Humana Press 1993), and by Cooper et al., "PCR-Based Full-Length cDNA Cloning Utilizing the Universal-Adaptor/Specific DOS Primer-Pair Strategy," Id. at pages 305–316.

Cloned antisense fragments are cleaved from the cloning vector and inserted into an expression vector. For example, HindIII and XbaI can be used to cleave the antisense fragment from TA cloning vector pCR™-II (Invitrogen;San Diego, Calif.). Suitable expression vectors typically contain (1) prokaryotic nucleic acid elements coding for a bacterial origin of replication and an antibiotic resistance marker to provide for the amplification and selection of the expression vector in a bacterial host; (2) nucleic acid elements that control initiation of transcription, such as a promoter; and (3) nucleic acid elements that control the processing of transcripts, such as a transcription termination/polyadenylation sequence.

For a plant host, the transcriptional and translational regulatory signals preferably are derived from viral sources in which the regulatory signals are associated with a particular gene which has a high level of expression. Transcriptional regulatory sequences include a promoter region sufficient to direct the initiation of RNA synthesis. Suitable promoters include those described above for expression vectors in plants (e.g., CaMV and FMV).

Antisense polynucleotides according to the present invention are derived from any portion of the open reading frame of the Bin1 cDNA. Preferably, mRNA sequences (i) surrounding the translation initiation site and (ii) forming loop structures are targeted. Based upon the size of the human genome, statistical studies show that a nucleic acid segment approximately 14–15 base pairs long will have a unique sequence in the genome. To ensure specificity of targeting Bin1 RNA, therefore, it is preferred that the antisense polynucleotides are at least 15 nucleotides in length.

Not every antisense polynucleotide will provide a sufficient degree of inhibition or a sufficient level of specificity for the Bin1 target. Thus, it will be necessary to screen polynucleotides to determine which have the proper antisense characteristics. A preferred method to assay for a useful antisense polynucleotide is the inhibition of protein kinase activity or inhibition of steroid binding.

The above approaches can also be used not only with antisense nucleic acid, but also with ribozymes, or triplex agents to block transcription or translation of a specific Bin1 mRNA, either by masking that mRNA with an antisense nucleic acid or triplex agent, or by cleaving it with a ribozyme.

Use of an oligonucleotide to stall transcription is known as the triplex strategy since the oligomer winds around double-helical nucleic acid, forming a three-strand helix. Therefore, these triplex compounds can be designed to recognize a unique site on a chosen gene (Maher, et al., *Antisense Res. and Dev.*, 1(3):227, 1991; Helene, C., *Anti-cancer Drug Design*, 6(6):569, 1991).

Ribozymes are RNA molecules possessing the ability to specifically cleave other single-stranded RNA in a manner analogous to nucleic acid restriction endonucleases. Through the modification of nucleotide sequences which encode these RNAs, it is possible to engineer molecules that recognize specific nucleotide sequences in an RNA molecule and cleave it (Cech, *J.Amer.Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

BIN1 AS A CONTRACEPTIVE

Homologues of plant Bin1 may play a role in regulation of the menstrual cycle or regulation of uterine function during pregnancy, and therefore, Bin1, anti-Bin1 antibodies, or antisense polynucleotides may be useful either in contraceptive regimens, in enhancing the success of in vitro fertilization procedures, or in preventing premature labor. The methods described herein can be used for administration of Bin1 or Bin1 agents for such purposes.

The invention also includes various pharmaceutical compositions that block binding of brassinosteroids or hormones to Bin1. The pharmaceutical compositions according to the invention are prepared by placing an antibody against Bin1, a peptide or peptide derivative of Bin1, a Bin1 mimetic, or a Bin1-binding agent according to the present invention into a form suitable for administration to a subject using carriers, excipients and additives or auxiliaries.

The above disclosure generally describes the present invention. A more complete understanding can be obtained by reference to the following specific examples which are provided herein for purposes of illustration only and are not intended to limit the scope of the invention.

EXAMPLES

Example 1

CLONING OF BIN1 POLYNUCLEOTIDE

The following protocol was utilized for cloning plant Bin1 polynucleotide. Eighteen new Arabidopsis dwarf mutants were identified that lacked the ability to respond to brassinolide and were named bin mutants. The bin1 mutations were used to map the gene to a small interval on Arabidopsis chromosome 4. Bin1 was cloned using the standard methods of map-based cloning. The Bin1 encoding polynucleotide was identified within this interval by sequencing the wild type and mutant alleles of this nucleic acid. All mutant DNAs contain a mutation in the Bin1 coding sequence thereby establishing that this interval contained the Bin1 gene. (See Li et al., *Science* 272:398, 1996).

Example 2

COMPARISON OF BIN1 WITH OTHER RECEPTOR KINASES

A BLAST search was performed using the sequence of SEQ ID NO:1. Several receptors and receptor-like protein kinases (e.g., serine/threonine) sequences having homology to Bin1 were identified, both in plant species as well as in non-plant species. Some of those sequences are listed below:

ERECTA (Arabiclopsis)

CLV1 receptor kinase (Arabidopsis)

AWJL218 protein (wheat)

Pto Kinase interactor 1

ARK2 product

Protein kinase S50767 (rice)

Maize putative receptor protein kinase ZMP

AWJL236 protein (wheat)

Ipomoea trifida receptor

Interleukin-1 receptor associated kinase (human)

Although the invention has been described with reference to the presently preferred embodiments, it should be understood that various modifications can be made without departing from the spirit of the invention. Accordingly, the invention is limited only by the following claims.

What is claimed is:

1. An isolated polynucleotide encoding Bin1 polypeptide as set forth in SEQ ID NO:2.

2. An isolated polynucleotide selected from the group consisting of:
   a) SEQ ID NO:1;
   b) SEQ ID NO:1, wherein T can also be U;
   c) nucleic acid sequences fully complementary to a) or b); over the full length of a) or b), respectively; and
   d) an isolated polynucleotide that hybridizes to a) or b) under conditions of 0.1×SSC at about 68 degrees C. wherein said hybridizing polynucleotide encodes a Bin1 polypeptide.

3. The polynucleotide of claim 1, wherein the polynucleotide is isolated from a plant cell.

4. A recombinant expression vector comprising a polynucleotide sequence according to claim 1.

5. A host cell containing the vector of claim 4.

6. A method of producing a genetically modified plant having increased yield as compared to a wild-type plant, said method comprising:

introducing at least one nucleic acid sequence encoding a Bin1 polypeptide as set forth in SEQ ID NO:2 into a plant cell to obtain a transformed plant cell, said nucleic acid sequence operably associated with a promoter; producing a plant from said transformed plant cell under conditions which allow expression of Bin1 polypeptide; and selecting a plant exhibiting said increased yield.

7. The method of claim 6, wherein said introducing is by physical means.

8. The method of claim 6, wherein said introducing is by chemical means.

9. The method of claim 6, wherein the plant cell is selected from the group consisting of protoplasts, gamete producing cells, and cells which regenerate into whole plants.

10. The method of claim 6, wherein the promoter is selected from the group consisting of a constitutive promoter and an inducible promoter.

11. A plant produced by the method of claim 6, wherein the plant comprises at least one nucleic acid sequence encoding a Bin1 polypeptide as set forth in SEQ ID NO:2.

12. Plant tissue derived from a plant produced by the method of claim 6, wherein the tissue comprises at least one nucleic acid sequence encoding a Bin1 polypeptide as set forth in SEQ ID NO:2.

13. A seed derived from a plant produced by the method of claim 6, wherein the seed comprises at least one nucleic acid sequence encoding a Bin1 polypeptide as set forth in SEQ ID NO:2.

14. A method for genetically modifying a plant cell such that a plant, produced from said cell, has increased yield as compared with the wild-type plant, said method comprising:

introducing a polynucleotide encoding the Bin1 polypeptide as set forth in SEQ ID NO:2 into a plant cell to obtain a transformed plant cell; and growing the transformed plant cell under conditions which permit inducing or augmenting of Bin1 polypeptide expression thereby producing a plant having increased yield.

15. The method of claim 14, wherein said increased yield is achieved by inducing expression of bin1 in the plant.

16. The method of claim 14, wherein said increased yield is achieved by augmenting expression of bin1 in the plant.

17. A method for identifying an agent that binds to the Bin1 polypeptide set forth in SEQ ID NO:2, comprising:

a) contacting a cell expressing Bin1 polypeptide and a suspected Bin1 binding agent under conditions and for such time as to allow binding;

b) separating a complex of Bin1 polypeptide and said binding agent from unbound Bin1 polypeptide; and c) isolating the agent.

18. A method of producing genetically transformed, disease resistant plants, comprising:

a) introducing into the genome of a plant cell to obtain a transformed plant cell, a nucleic acid construct comprising:

(i) a promoter which functions in plant cells to cause the production of an RNA sequence; and (ii) a nucleic acid coding sequence that encodes Bin1 polypeptide as set forth in SEQ ID NO:2; and b) regenerating from the transformed plant cells genetically transformed plants which express Bin1 polypeptide in an amount effective to inhibit infection by a bacterial or fungal pathogen.

19. The method of claim 18, wherein said nucleic acid sequence comprises SEQ ID NO:1.

20. The method of claim 18, wherein said promoter is selected from FMV35S and CaMV35S promoters.

21. The method of claim 18, wherein said promoter is induced by pathogen infection.

22. A genetically transformed, disease resistant plant comprising a recombinant nucleic acid sequence containing in operative linkage:

a) a promoter which functions in plant cells to cause the production of an RNA sequence; and b) a polynucleotide sequence that encodes a Bin1 polypeptide set forth in SEQ ID NO:2.

23. The plant of claim 22, wherein said promoter is selected from FMV35S and CaMV35S promoters.

24. The plant of claim 22, wherein said promoter is induced by pathogen infection.

25. The plant of claim 22, wherein said polynucleotide sequence comprises SEQ ID NO:1.

26. A method for inhibiting the expression of a polynucleotide encoding a Bin1 polypeptide set forth in SEQ ID NO:2 in a plant cell comprising contacting a polynucleotide encoding a Bin1 polypeptide with an inhibiting effective amount of an antisense oligonucle-otide that binds to a segment of the polynucleotide, wherein binding of the antisense oligonucleotide to the polynucleotide inhibits Bin1 polypeptide expression.

27. An isolated Arabidopsis polynucleotide encoding Bin1 polypeptide.

28. The isolated polynucleotide of claim 27, wherein said polynucleotide comprises SEQ ID NO: 1.

* * * * *